United States Patent
Rao

(10) Patent No.: US 12,274,496 B2
(45) Date of Patent: Apr. 15, 2025

(54) METHODS FOR PHOTOACOUSTIC TEMPERATURE MEASUREMENT

(71) Applicant: Bin Rao, Saint Louis, MO (US)

(72) Inventor: Bin Rao, Saint Louis, MO (US)

(73) Assignee: Bin Rao, Saint Louis, MO (US)

( * ) Notice: Subject to any disclaimer, the term of this patent is extended or adjusted under 35 U.S.C. 154(b) by 1058 days.

(21) Appl. No.: 17/021,902

(22) Filed: Sep. 15, 2020

(65) Prior Publication Data
US 2021/0059752 A1   Mar. 4, 2021

Related U.S. Application Data

(62) Division of application No. 15/881,748, filed on Jan. 27, 2018, now Pat. No. 10,806,513.

(51) Int. Cl.
| | | |
|---|---|---|
| A61B 8/00 | (2006.01) | |
| A61B 5/00 | (2006.01) | |
| A61B 18/20 | (2006.01) | |
| A61B 18/22 | (2006.01) | |
| A61B 18/00 | (2006.01) | |
| A61N 5/067 | (2006.01) | |

(52) U.S. Cl.
CPC .......... *A61B 18/203* (2013.01); *A61B 5/0095* (2013.01); *A61B 18/22* (2013.01); *A61B 2018/00005* (2013.01); *A61B 2018/00458* (2013.01); *A61N 5/067* (2021.08)

(58) Field of Classification Search
CPC ........ A61B 18/203; A61B 2018/00005; A61B 5/0095
See application file for complete search history.

(56) References Cited

U.S. PATENT DOCUMENTS

| | | | |
|---|---|---|---|
| 4,303,343 | A | 12/1981 | Patel |
| 5,759,200 | A | 6/1998 | Azar |
| 5,840,023 | A | 11/1998 | Oraevsky |
| 6,309,352 | B1 | 10/2001 | Oraevsky |
| 7,322,972 | B2 | 1/2008 | Viator |
| 2002/0019625 | A1 | 2/2002 | Azar |
| 2015/0216420 | A1 | 8/2015 | Oraevsky |

(Continued)

FOREIGN PATENT DOCUMENTS

WO    WO2013033145 A1    3/2013

OTHER PUBLICATIONS

Adams et al., "Thermal diffusivity and thickness measurements for solid samples utilizing the optoacoustic effect," The Analyst 102,678 (1977).

(Continued)

*Primary Examiner* — Joel Lamprecht

(57) ABSTRACT

TEMPERATURE MEASUREMENTS ARE CRITICAL TO VARIOUS ENERGY BASED THERAPEUTIC SYSTEMS, INCLUDING LASER, LIGHT, ELECTROMAGNETIC WAVE, AND HIGH INTENSITY FOCUSED ULTRASOUND BASED THERAPEUTIC SYSTEMS. THIS INVENTION DISCLOSES TECHNIQUES, APPARATUS AND METHODS FOR TEMPERATURE MEASUREMENTS OF SURGICAL TARGETS DURING VARIOUS THERAPEUTIC INTERVENTIONS WITH PHOTOACOUSTIC METHODS, ESPECIALLY WHEN DYNAMIC TEMPERATURE PULSES ARE GENERATED BY SELECTIVE PHOTOTHERMOLYSIS.

2 Claims, 18 Drawing Sheets

(56) References Cited

U.S. PATENT DOCUMENTS

2017/0014317 A1     1/2017    Youngbull

OTHER PUBLICATIONS

Barua et al., "Laser-tissue interaction in tattoo removal by Q-switched lasers ," J Cutan Aesthet Surg 8, 5-8(2015).

Bernstein, "Laser Tattoo Removal," Seminars in Plastics Surgery 21, 175-192(2007).

C. T. Andrew, "Applications of photoacoustic sensing techniques," Rev. Mod. Phys. 58, 381-431(1986).

Cox et al., "Quantitative spectroscopic photoacoustic imaging: a review," Journal of Biomedical Optics 17(6), 061202 (2012).

Esenaliev et al., "Real-time optoacoustic monitoring of temperature in tissues", Proc. SPIE 3601, Laser-Tissue Interaction X: Photochemical, Photothermal, and Photomechanical(1999).

Gary A. West, "Photoacoustic spectroscopy," Review of Scientific Instruments 54, 797 (1983).

Hordvik et al., "Photoacoustic technique for determining optical absorption coefficients in solids," Applied Optics 16, 101-107 (1977).

Larin et al., "Monitoring of temperature distribution in tissues with optoacoustic technique in real time", Proc. SPIE 3916, Biomedical Optoacoustics(2000).

Liu et al., "In vivo, high-resolution, three-dimensional Imaging of port wine stain microvasculature in human skin," Lasers in Surgery and Medicine 45, 626-632(2013).

Maslov et al., "Optical-resolution photoacoustic microscopy for in vivo imaging of single capillaries", Optics Letters 33, 929-931(2008).

Maslov et al., "In vivo dark-field reflection-mode photoacoustic microscopy," Optics Letters 30, 625-627(2005).

Nelson et al., "Imaging blood flow in human port-wine stain in situ and in real time using optical Doppler tomography," Arch Dermatol. 137, 741-744(2001).

Ortiz et al., "Port-wine stain laser treatment and novel approaches," Facial Plast Surg 28, 611-620(2012).

Peach et al., "Colour shift following tattoo removal with Q-switched Nd-YAG laser (1064/532)," British Journal of Plastic Surgery 52,482-487(1999).

Rao et al., "Smart laser treatment of port-wine stain in children," NIH grant abstract, published on Aug. 1, 2012. [retrieved on Jan. 26, 2018]. Retrieved from the Internet:< URL: http://grantome.com/grant/NIH/K99-AR062530-01>.

Shah et al., "Photoacoustic imaging and temperature measurement for photothermal cancer therapy," Journal of Biomedical Optics 13(3), 034024(2008).

Viator et al., "In vivo port-wine stain depth determination with a photoacoustic probe," Appl. Opt. 42, 3215-3224 (2003).

Wang, "Prospects of photoacoustic tomography," Medical Physics 35, 5758 (2008).

Wenzel, "Current concepts in laser tattoo removal," Skin Therapy Letter 15, 3-5(2010).

Zapka et al., "Noncontact optoacoustic monitoring of flame temperature profiles," Optics Letters 7, 477-479 (1982).

Zhang et al., "Backward-mode multiwavelength photoacoustic scanner using a planar Fabry-Perot polymer film ultrasound sensor for high-resolution three-dimensional imaging of biological tissues," Applied Optics 47,561-577 (2008).

METHODS FOR PHOTOACOUSTIC TEMPERATURE MEASUREMENT

CROSS-REFERENCE TO RELATED APPLICATIONS

This application is a divisional application of application Ser. No. 15/881,748, filed on Jan. 27, 2018, and entitled METHODS AND APPARATUS FOR OPTIMIZING SELECTIVE PHOTOTHERMOLYSIS, which is incorporated herein by reference.

BACKGROUND OF THE INVENTION

This document relates to surgery techniques, apparatus and methods, including surgery techniques, apparatus and methods for selective photothermolysis (SP) surgeries. Some techniques can be applied to general surgical systems that heat up lesions in tissue, including high-intensity-focused-ultrasound therapies.

SP, as described by Anderson and Parrish in a paper published by SCIENCE in 1983, utilizes short laser pulses to precisely control collateral thermal or mechanical damages around light-absorptive lesions without the need of aiming a laser micro-beam at surgical targets. SP could target not only nature chromophores within vasculature, skin, retina and other human tissues but also labeled single cells and their ultra-structures if both a tunable laser and cell-specific dye delivery system are available. A SP laser surgery has two distinct features, a large surgical area and a short surgical laser pulse that deposits most of the laser pulse energy into surgical targets. Thus non-surgical targets within a large surgical area remain healthy after SP while all surgical targets are damaged. In contrast, laser surgeries of non-SP category include laser surgeries that use continuous wave (CW) laser to photocoagulate surgical targets without limiting damaging area and laser surgeries that use a small, high energy laser beam to non-selectively evaporate or sublime all illuminated tissue or tissue at the laser beam focus. Typical non-SP laser surgery examples include photothermal cancer therapy with CW lasers, laser-assisted in-situ keratomileusis eye surgery, and femtosecond laser-assisted cataract surgery. Typical SP laser surgery examples include laser treatment of vascular malformation, some laser retinal photocoagulation surgeries, and some aesthetical laser surgeries such as laser tattoo removal.

Technical challenges associated with a SP laser surgery include maximizing laser energy deposition ratios of surgical targets to nature chromophores, confining laser energy deposition into surgical targets, and optimizing laser pulse energy. Non-optimized SP laser parameters are associated with unsatisfactory laser surgical outcomes. Although the compromised SP laser surgical outcomes are well-known for decades, no good solution exists in the prior art of SP.

BRIEF SUMMARY OF THE INVENTION

This document relates to surgery techniques, apparatus and methods for optimizing selective photothermolysis (SP) surgeries. Some techniques can be applied to general surgical systems that heat up lesions in tissue, including high-intensity-focused-ultrasound therapies. It is noted that a tunable light pulse in this document broadly means a light pulse with tuning capabilities in its central wavelength, or light pulse width, or light pulse energy, or a combination of them.

In one aspect, a pulsed light SP surgical system comprises a tunable pulsed light source to produce pulsed surgical light beam under the control of its control system; and a patient interface operable to be in contact with the target tissue. The patient interface comprises a light delivery unit, an acoustic detector, and an interface medium. The light delivery unit shapes the light beam profile, delivers light beam with an articulated arm, adjusts the light beam diameter, and transmits the light beam through the interface medium to a tissue surface. The pulsed light beam excites photoacoustic waves that propagate through the interface medium and are detected by the acoustic detector. The detected photoacoustic signals are digitized, analyzed by the control system for the generation of surgical light pulses with optimal central wavelength and light pulse energy for optimal SP surgical outcome.

In another aspect, a pulsed light SP surgical system comprises a tunable pulsed light source that can produce a pulsed surgical light beam or a pulsed or modulated temperature-sensing light beam or both under the control of its control system; and a patient interface operable to be in contact with the target tissue. The patient interface comprises a light delivery unit, an acoustic detector, and an interface medium. The light delivery unit shapes beam profiles of light beams, delivers light beams with an articulated arm, adjusts diameters of light beams, and transmits light beams through the interface medium to a tissue surface. The light beams excite photoacoustic waves that propagate through the interface medium and are detected by the acoustic detector. The detected photoacoustic signals are digitized, analyzed by the control system for the generation of surgical light pulses with optimal central wavelength, pulse width and pulse energy for optimal SP surgical outcome.

In another aspect, a surgical planning system comprises a tunable pulsed light source that can produce a subtherapeutic pulsed light beam or a pulsed or modulated temperature-sensing light beam or both under the control of its control system; and a patient interface operable to be in contact with the target tissue. The patient interface comprises a light delivery unit, an acoustic detector, and an interface medium. The light delivery unit shapes beam profiles of light beams, delivers light beams with an articulated arm, adjusts diameters of light beams, and transmits light beams through the interface medium to a tissue surface. The light beams excite photoacoustic waves that propagate through the interface medium and are detected by the acoustic detector. The detected photoacoustic signals are digitized, analyzed by the control system for determining optimal surgical light pulse parameters to be used by another conventional pulsed light SP surgical system.

In another aspect, a pulsed radiation SP surgical system comprises two tunable radiation sources; a patient interface operable to be in contact with the target tissue; and a control system. One tunable radiation source produces a pulsed surgical radiation for heating up lesions in tissue or extraneous contrast agents attached to lesions in tissue under the control of the control system. Another tunable radiation source produces a pulsed or modulated temperature-sensing radiation beam that can be absorbed by lesions in tissue or extraneous contrast agents attached to lesions in tissue for excitations of photoacoustic waves under the control of the control system. The patient interface comprises a radiation beam delivery unit for delivering radiation beams to tissue, and an ultrasonic detector to acquire photoacoustic signals excited by radiation beams. The control system acquires information from the ultrasonic detector in the patient interface, analyzes information, and controls the generation of radiation beams with optimal central wavelength or central frequency, pulse width, and pulse energy for optimal SP surgical outcome.

In another aspect, a method for tuning surgical laser wavelength and optimizing SP laser treatment of unknown surgical targets comprises determining a series of surgical wavelength points for spectroscopic scanning and setting up both patient interface and acoustic detector; sending out multiple subtherapeutic surgical laser pulses for each wavelength, acquiring and averaging photoacoustic signals, and repeating for all wavelength points; reconstructing 2-D, depth-resolved, relative extinction coefficient information for all wavelength points; calculating relative extinction coefficient curve for all absorbers, and identifying unknown surgical targets; calculating relative energy deposition ratio curves of unknown surgical targets to nature chromophores; and determining optimal surgical wavelengths for different types of surgical targets.

In another aspect, a method for calibration of the temperature-dependent relative logarithm function of Grüneisen parameter of tissue comprises measuring the equilibrium temperature of tissue; measuring the photoacoustic signals of a surgical target excited by a temperature-sensing laser pulse with a constant laser pulse energy; calculating a baseline signal as the logarithm of the amplitude of the photoacoustic signal at the equilibrium temperature; sending only a surgical laser pulse and measuring excited photoacoustic signals; sending both a surgical laser pulse and a temperature-sensing laser pulse, and measuring the excited photoacoustic signals by dual pulses; calculating the logarithm of the amplitude of the photoacoustic signal excited by the temperature-sensing laser pulse after a subtraction operation and a logarithm operation; acquiring a data point after subtracting the baseline signal from the logarithm of the amplitude of the photoacoustic signal excited by the temperature-sensing laser pulse; determining whether there is a laser-induced cavitation; if not, waiting for temperature returns to equilibrium; increasing surgical laser pulse to ki times; repeating the above procedures to acquire more data points for the relative logarithm function of Grüneisen parameter of tissue until a laser-induced cavitation is observed; calculating absolute temperature rise caused by surgical laser pulses and fitting the curve of the relative logarithm function of Grüneisen parameter of tissue with enough data points.

In another aspect, a method for photoacoustic sensing of the dynamic temperature of a surgical target in a tissue at the end of a short surgical laser pulse comprises measuring body temperature before laser surgical intervention; sending a temperature sensing laser pulse with a constant laser pulse energy, measuring the amplitude of the excited photoacoustic signal and calculating its logarithm as a baseline signal; sending only a surgical laser pulse and measuring the excited photoacoustic signal; sending both the surgical laser pulse and the temperature-sensing laser pulse at the end of the surgical laser pulse, and measuring the excited photoacoustic signal by dual pulses; calculating the photoacoustic signal amplitude excited by the temperature-sensing laser pulse at an unknown temperature at the end of the surgical laser pulse; separating the temperature-dependent part from other temperature-independent parts with a logarithm operation; calculating the relative logarithm function value by subtracting the baseline signal; determining the unknown temperature at the end of the surgical laser pulse from the calibrated relative logarithm function of Grüneisen parameter of tissue; and ending the temperature sensing operation.

In another aspect, a method for measuring thermal relaxation time of a surgical target in tissue comprises measuring the body temperature and the photoacoustic signal of a surgical target at body temperature with a temperature-sensing laser pulse and calculating the logarithm of the photoacoustic signal amplitude as a base line signal; sending a subtherapeutic surgical laser pulse and measuring excited photoacoustic signal; sending both the subtherapeutic surgical laser pulse and the temperature-sensing laser pulse with a precise delay time, measuring excited photoacoustic signal of dual pulses, and calculating the amplitude of the photoacoustic signal excited by the temperature-sensing laser pulse; separating the temperature-dependent part from other temperature independent parts with a logarithm operation and calculating the relative logarithm function value by subtracting the baseline signal; determining the temperature of the surgical target at the precise delay time; waiting until surgical target temperature returns to body temperature; determining whether enough delay time points have been acquired for a curve-fitting; if not, repeating the above procedure for measuring temperature at another delay time until enough delay time points have been acquired; fitting the curve of temperature versus delay time and determining thermal relaxation time of the surgical target; and ending the thermal relaxation time measurement operation.

In another aspect, a method for optimizing the surgical laser pulse energy during a laser photocoagulation surgery comprises selecting a surgical target; measuring the surgical target's thermal relaxation time; optimizing surgical laser pulse width according to the surgical target's thermal relaxation time; sending only the surgical laser pulse and measuring the excited photoacoustic signal by the surgical laser pulse; sending both the surgical laser pulse and the temperature-sensing laser pulse and measuring the excited photoacoustic signal by dual pulses; calculating the amplitude of the photoacoustic signal excited by the temperature-sensing laser pulse; separating the temperature-dependent part with a logarithm operation; calculating relative logarithm function value by subtracting the baseline signal acquired in the thermal relaxation time measurement step; determining the temperature of the surgical target; determining whether the temperature reaches a predetermined surgical temperature of photocoagulation; if not, waiting for temperature recovery to body temperature and increasing surgical laser pulse energy; repeating the above temperature measurement procedure until the temperature reaches the predetermined surgical temperature of photocoagulation; and ending the optimization of surgical laser pulse energy during a laser photocoagulation surgery.

In another aspect, a method for optimizing the surgical laser pulse energy during a laser photodisruption surgery comprises selecting a surgical target; sending the surgical laser pulse; measuring the excited photoacoustic signal; drawing one point for the curve of photoacoustic signal amplitude versus laser pulse energy; determining whether there is a laser-induced cavitation; if not, waiting for temperature recovery to body temperature, increasing surgical laser pulse energy, and repeating the above procedure from the second step until the laser-induced cavitation is observed and the surgical laser pulse energy is optimized.

In another aspect, a method for determining the surgical laser pulse energy to achieve a predetermined temperature without laser surgery comprises selecting a surgical target; measuring the surgical target's thermal relaxation time; optimizing surgical laser pulse width according to the surgical target's thermal relaxation time; sending a subtherapeutic surgical laser pulse and measuring excited photoacoustic signal; sending both the subtherapeutic surgical laser pulse and the temperature-sensing laser pulse; measuring excited photoacoustic signal by dual pulses; calculating the amplitude of the photoacoustic signal excited by the temperature sensing laser pulse; separating the temperature-dependent part with a logarithm operation and calculating relative logarithm function value by subtracting the baseline signal acquired in previous thermal relaxation time measurement step; calculating the dynamic temperature rise due to the subtherapeutic surgical laser pulse and the required surgical laser pulse energy for heating the surgical target to a predetermined temperature; and ending the optimization of surgical laser pulse energy to achieve a predetermined temperature without laser surgery.

In yet another aspect, a method for an optimized SP laser surgery with skin cooling comprises tuning the surgical laser wavelength to maximize SP surgical effects; optimizing surgical laser pulse width; optimizing surgical laser pulse energy; measuring body temperature; applying a temperature-sensing laser pulse; measuring excited photoacoustic signal of an epidermis target; adjusting skin cooling parameter; applying skin cooling and a delayed temperature-sensing laser pulse; measuring temperature of the epidermis target; determining whether the epidermis target has been cooled to a predetermined temperature; if not, returning to the above procedure of adjusting skin cooling parameter and measuring epidermis target temperature until it is cooled to a predetermined temperature; and performing an optimized SP laser surgery.

DETAILED DESCRIPTION OF THE INVENTION

Figure 1:
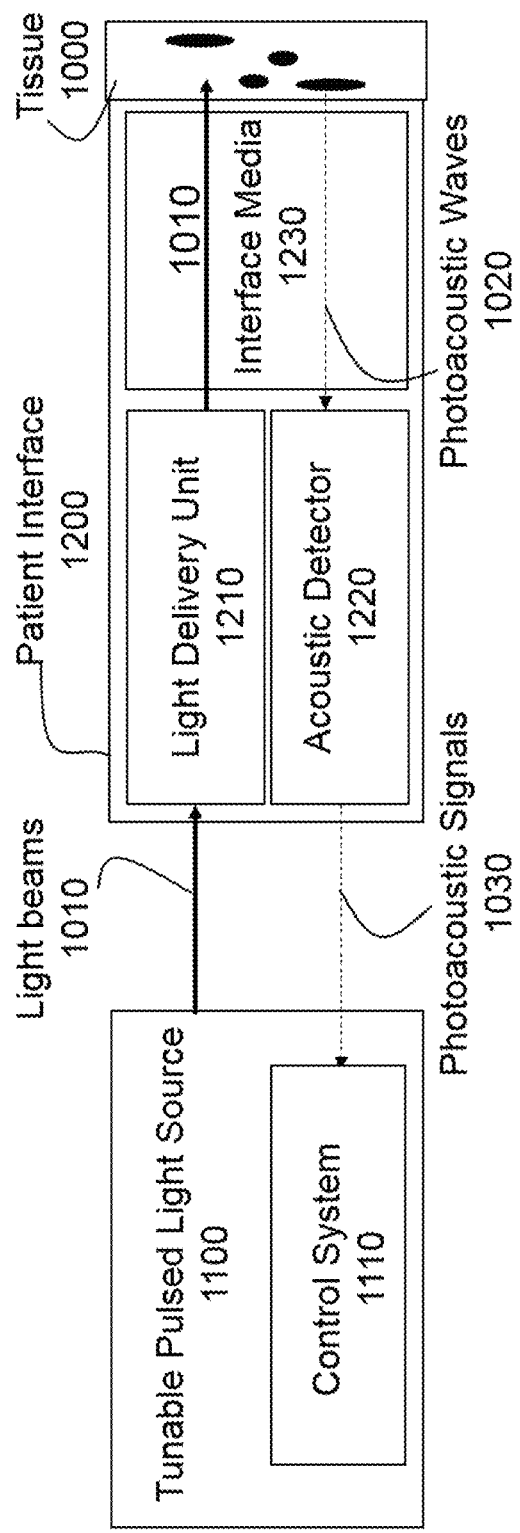
FIG. 1 shows an example of a pulsed light selective photothermolysis (SP) surgical system wherein the inclusion of an acoustic detector is the key for optimizing SP.

It is important to understand laser-tissue interaction mechanisms of selective photothermolysis (SP) laser surgery before addressing its clinical problems. Both thermal and mechanical damages could be utilized in SP. Initially, no measurable effects could be caused when tissue temperature is elevated to 37°-42° C. by SP laser pulses. Tissue is in hyperthermia status when temperature keeps rising to 42°-50° C. A large portion of tissue might undergo necrosis if the hyperthermia lasts for several minutes. Enzyme activity reduction and cell immobility start from 50° C. Denaturation of proteins and collagen occurs at 60° C. and leads to coagulation of tissue and necrosis of cells. Cell membrane permeability will significantly increase at 80° C. Water molecules will be vaporized at 100° C. It may lead to cavitation and tissue mechanical rupture by acoustic shock-waves associated with the laser-induced cavitation. Another type of mechanical damage could be caused by the strong photoacoustic waves generated by light absorbers upon the short laser pulse excitations. Major SP commercial applications include laser tattoo removal, laser treatment of vascular malformation and laser retinal photocoagulation.

Laser tattoo removal is usually performed with very short laser pulses in nanosecond or even picosecond regime. However, the proposed mechanisms behind laser tattoo removal have their physical, chemical and biological origins. Pigmented particles of tattoo will experience rapid temperature rise and volume expansion upon the energy deposition or excitation by a short laser pulse. However, most of the temperature rise and the volume expansion will be lost after a short period of time, determined by thermal relaxation time (time taken for 50% of heat energy to be dissipated away) of these particles. Photoacoustic waves are generated along with the volume changes of these particles. Laser energy is transformed into both thermal energy and mechanical energy carried by the photoacoustic waves. In many cases, large laser pulse energy absorbed by pigmented particles may cause optical breakdown, plasma generation, chemical reactions between plasma and pigmented particles, cavitation and generation of acoustic shock-waves. These pigmented particles might be pyrolytically altered or shattered into smaller particles by the photoacoustic waves and acoustic shock-waves. Hosting cell necrosis and surround tissue damage might be induced thermally and mechanically during this process. In the end, the wound healing process might remove partial pigmented particles through rephago-cytosis and alter the dermal scattering coefficients of the affected tissue, which might make the deeper pigmented particles less visible.

For laser tattoo removal application, the color of a tattoo depends on many factors including its optical absorption spectrum, optical scattering and absorption coefficients of the tissue above and below the pigments, the depth of the pigment and anatomical location of the pigments. It was reported that tattoos with significantly different optical absorption spectra could present themselves with the same color to naked eyes. Obviously, current practice of selecting surgical laser wavelength based on the color of a tattoo is not justified. On the other hand, there are only a handful of laser wavelengths (694 nm ruby laser, 755 nm Alexandrite, 1064 nm Nd:YAG and 532 nm second harmonic Nd:YAG) available in the market for laser tattoo removal. Even if the absorption spectra of the pigments of the tattoo is happened to be known, there are significant chances that it is not matching with any existing laser in the market. Anderson and Parrish envisioned a tunable laser for SP in 1983. However, such a laser is not available yet because nobody knows what wavelength should be adjusted to. Additionally, the selection of treatment laser pulse energy is also determined by the clinician's experience. Both clinical problems of laser tattoo removal are addressed by this invention.

Laser treatment of vascular malformation starts from the argon laser (488 and 514 nm) treatment of port-wine stain (PWS) in 1970s. The blue-green light of argon lasers is preferentially absorbed by hemoglobin within the PWS blood vessels. The deposited laser pulse energy into the vessels is largely converted to heat, causing thrombosis and destruction of the PWS blood vessels. The first generation argon laser had relatively long pulse duration (~0.01 s), which caused non-specific tissue thermal damage of epidermis tissue. Thus, scarring was a frequent complication of the first generation argon laser treatment of PWS. Selective photothermolysis of PWS blood vessels was achieved by the first generation pulsed dye laser (PDL) (577 nm or 585 nm, 0.45 milliseconds) that selectively photocoagulated PWS blood vessels and spared overlying epidermal tissue with a low incidence of side effects. As PDL laser energy is deposited in the intraluminal blood due to selective absorption of hemoglobin, the heat diffuses to the vessel wall and causes vascular wall necrosis and subsequent extravasation of red blood cells into the adjacent dermis. Dermal collagen fills the space of photocoagulated PWS vessels via wound healing process. The removal of photocoagulated PWS lesions leads to the blanching of PWS. The second generation PDL technique adopts larger spot sizes, higher energy densities, variable pulse durations, and dynamic cooling for more effective treatment of PWS. Currently, the second generation PDL with dynamic pulse duration and dynamic epidermal cooling by liquid cryogen sprays is the treatment of choice for PWSs. However, the laser has to be operated by experienced clinicians who adjust laser pulse width and laser pulse energy based on their experiences. In fact, the average success rate for full clearance is below 20%. The selection of pulsed laser parameters is the most challenging clinical problem in laser treatment of vascular malformation.

The above mentioned clinical problems in laser tattoo removal and laser treatment of vascular malformation are obviously related to the distributions of light absorbers inside of tissue. Some experienced clinician takes advantage of the sounds generated during laser and tissue interaction to help laser tattoo removal surgery. However, human only hears sound wave between 20 Hz-20,000 Hz. For laser tattoo removal, laser tissue interaction does generate high-frequency ultrasonic waves. Most of their frequency components are far beyond 20,000 Hz. In other words, most of useful information are completely ignored. By adding an ultrasonic detector to "hear" the responses from tissue under a SP laser surgery, this invention is able to address the above-mentioned clinical problems. The science behind the photoacoustic waves during laser-tissue interactions is photoacoustics, the key technique for this invention.

Photoacoustic techniques originate from Alexander Graham Bell who discovered photoacoustic effect in 1880. The generation of photoacoustic wave consists of the following stages including conversion of the absorbed pulsed or modulated radiation into heat energy, temporal change of temperature that rises as laser pulse energy is absorbed and falls when laser pulse ends and the heat dissipates, and volume expansion and contraction following these temperature changes, which generate pressure changes (i.e. photoacoustic wave). Hordvik et al. reported photoacoustic technique for determining optical absorption coefficients in solids in 1977. Photoacoustic spectroscopy was applied to a wide variety of conventional spectroscopic measurements as reviewed by West et al. in 1983. More recent developments of photoacoustic techniques were motivated by biomedical imaging applications. Major photoacoustic technique developments in the biomedical imaging field include the inventions of acoustic-resolution & optical-resolution photoacoustic microscopies by Maslov et al. and the Fabry-Perot photoacoustic sensor based photoacoustic tomography by Zhang et al. The significantly improved image performance (sensitivity, resolution, depth and speed) of the above photoacoustic imaging systems and improvements of acoustic transducer arrays by industry for various photoacoustic tomography configurations generate high impacts in biology and medicine.

The penetration of photoacoustic techniques into SP laser surgery is very limited. Nobody tried to build a wavelength tunable laser and apply such a laser for tattoo removal with photoacoustics. Selecting laser wavelength in laser treatment of vascular malformation might be less critical than in laser tattoo removal. But it is still a very challenging task to optimize other parameters of laser surgical systems for laser treatment of vascular malformation. In fact, a SP laser surgery does not necessary get rid of surgical targets or change the spatial location of surgical targets right after a SP laser surgery. It requires a long wound healing process to remove damaged tissues through rephagocytosis. Photoacoustic imaging of lesions before and right after SP laser surgery almost presents no changes in lesion images. Thus, a simple photoacoustic imaging of lesions has no value for optimizing SP laser surgery. Viator et al. demonstrated the feasibility of imaging deep port-wine stain lesions with photoacoustic tomography without further application of the acquired lesion depth information for optimizing laser treatment of port-wine stain. In order to optimize laser treatment of port-wine stain in children, Rao et al. proposed to image the port-wine stain vessel size and depth in child patients with optical-resolution photoacoustic microscopy, construct physical model of port-wine stain lesions with lesion information, and derive optimal laser treatment parameters (pulse width and pulse energy) with massive computer simulations. Other imaging modalities such as optical Doppler tomography and optical coherence angiography relied on blood flow or blood flow induced optical speckles to acquire information of port-wine stain lesions. However, the lack of blood flow right after laser surgery could not confirm full photocoagulation of lesion vessels. It was hypothesized that partially coagulated lesion vessels could remain refractory after laser treatment. Another limitation of these optical imaging modalities is their shallow imaging depth of 1-2 mm. In contrast, this invention takes simple experimental approaches to address the SP clinical problems.

The disclosed techniques, methods and apparatus of this invention are based on the physical principle of photoacoustic effect and its temperature-dependence. In early literature of photoacoustic techniques, the temperature-dependent photoacoustic effect was utilized in a range of temperature related measurements including measuring flame temperature and measuring solid thermal diffusivity. Esenaliev et al. reported real-time optoacoustic monitoring of temperature in ex vivo canine tissues in 1999. Larin et al. reported optoacoustic laser monitoring of cooling and freezing of ex vivo canine liver in 2002. Shah et al. reported photoacoustic temperature monitoring of ex vivo porcine tissue in 2008. Oraevsky et al. described optoacoustic imaging methods for medical diagnosis and real time optoacoustic monitoring of change in tissue properties, and an improved temperature calibration method in U.S. Pat. Nos. 5,840,023A, 6,309,352B1, and US2015/0216420A1. In a continuous-wave laser thermal therapy described by Oraevsky et al., tissue temperature varies very slowly. The continuous-wave laser has no effect on an asynchronous photoacoustic temperature-sensing process. In contrast, short surgical light pulses of a SP surgery system heat up a surgical target within its short pulse duration and the surgical target cools down quickly. Measuring a dynamic temperature rise due to energy deposition of a short surgical laser requires the temperature-sensing light pulse to be synchronized to the surgical light pulse with an exact short time delay. Additionally, the strong surgical light pulses generate strong photoacoustic signals upon absorption by light absorbers in tissue. The photoacoustic signal excited by the surgical light pulse interferes with the photoacoustic signal excited by the temperature-sensing light pulse. Both issues, which make the photoacoustic temperature measurement methods described by Oraevsky et al. and others in prior art invalid for SP surgeries with short surgical light pulses, are addressed by methods of this invention.

In summary, the prior art is deficient in methods to address clinical problems in SP surgeries such as laser tattoo removal and laser treatment of vascular malformation. The surgery techniques, apparatus and methods are disclosed below to fill the gaps between the science theory of SP and clinical practices.

As an example, FIG. 1 shows an example of a revolutionary, pulsed light SP surgical system wherein the inclusion of an acoustic detector differentiates it from a conventional SP light surgical system. This SP pulsed light surgical system comprises a tunable pulsed light source 1100 to produce light beams 1010 under the control of its control system 1110; and a patient interface 1200 operable to be in contact with a tissue 1000. In one implementation of FIG. 1, the light beams 1010 comprise only a surgical pulsed light beam. The pulse width of the pulsed light beam is less than $10^{-7}$ seconds, or less than $10^{-8}$ seconds, or less than $10^{-9}$ seconds in order to efficiently excite photoacoustic signals. The patient interface 1200 comprises a light delivery unit 1210, an acoustic detector 1220, and an interface medium 1230. The light delivery unit 1210 shapes the light beam profile, delivers the light beam with an articulated arm, adjusts the light beam diameter and transmits the light beam through the interface medium 1230 to a tissue 1000 surface. The pulsed light beam 1010 excites photoacoustic waves 1020 that propagate through the interface medium 1230 and are detected by the acoustic detector 1220. The detected photoacoustic signals 1030 are digitized, analyzed in the control system 1110 for the control of the tunable pulsed light beam 1100. It is noted that a tunable light source in this document broadly means a light source with tuning capabilities in its central wavelength, or light pulse width, or light pulse energy or a combination of them. Tunable light source itself is not difficult to make. However, the missing part is how the central wavelength and other surgical light pulse parameters should be tuned according to surgical targets in tissue. The inclusion of an acoustic detector is exactly the missing part in prior art of SP surgeries. The inclusion of an acoustic detector makes sense to the utilization of a tunable light source in SP surgeries for the first time. Both the tunable light source and the acoustic detector make an optimized SP surgery possible, a goal that has been desired for decades.

In order to fully utilize the disclosed methods below for optimized SP surgical outcomes, it is desirable to utilize a more advanced tunable light source 1100, which can produce a surgical light pulse or a temperature-sensing light beam or both under the control of its control system 1110. For most of implementations of FIG. 1, the temperature-sensing light beam comprises temperature-sensing light pulses that have a tunable time delay relative to surgical light pulses. However, the temperature-sensing light beam could be an intensity modulated light beam to excite photoacoustic waves when depth-resolved tissue information is not required for an application, or a chirped intensity-modulated light beam to allow a very low-resolution depth discrimination. The pulse width of the temperature-sensing light pulses is less than $10^{-7}$ seconds, or less than $10^{-8}$ seconds, or less than $10^{-9}$ seconds in order to efficiently excite photoacoustic signals. The central wavelength and pulse width of the temperature-sensing light beam could be fixed for some implementations. The temperature-sensing light pulse energy is of subtherapeutic level. For the tunable light source 1100, its tuning capabilities should match with the needs of a specific SP surgery application. The most practical implementation of such a more advanced tunable light source is to integrate a tunable surgical light source unit and a tunable temperature-sensing light source unit into a single package with a shared power supply subsystem, a shared cooling subsystem and a shared control system 1110. The light beams of the light source units need to be combined, and sent out from the same light output port. In some implementations, it is preferable to use a low-cost, fixed-wavelength, pulsed solid state laser to generate the temperature-sensing light beam.

Yet another implementation of FIG. 1 could be a surgical planning system that provide optimized surgical laser parameters for other conventional pulsed light SP surgical systems. Such a surgical planning system comprises a tunable pulsed light source that can produce a subtherapeutic pulsed light beam or a pulsed or modulated temperature-sensing light beam or both under the control of its control system; and a patient interface operable to be in contact with the target tissue. The patient interface comprises a light delivery unit, an acoustic detector, and an interface medium. The light delivery unit shapes beam profiles of light beams, delivers light beams with an articulated arm, adjusts diameters of light beams, and transmits light beams through the interface medium to a tissue surface. The light beams excite photoacoustic waves that propagate through the interface medium and are detected by the acoustic detector. The detected photoacoustic signals are digitized, analyzed by the control system for determining optimal surgical light pulse parameters to be used by another conventional pulsed light SP surgical system. The advantage of such a surgical planning system is that its laser pulse repetition rate could be much higher than a surgical system and the time for acquiring optimized surgical laser parameters is much shorter.

The key of this invention is the inclusion of an ultrasonic transducer in a conventional SP surgery system. A pulsed light SP surgical system of FIG. 1 could be generalized as a pulsed radiation SP surgical system by replacing the surgical light pulse with any form of radiation (radio waves, microwaves, infrared light, visible light, Ultraviolet, X-rays, Gamma rays) pulse that heats up lesions or extraneous contrast agents attached to lesions in tissue, replacing the temperature-sensing light pulse with any form of pulsed or modulated radiation (radio waves, microwaves, infrared light, visible light, Ultraviolet, X-rays, Gamma rays) that can be absorbed by lesions in tissue or extraneous contrast agents attached to lesions in tissue, and effectively excite photoacoustic waves, and replacing the light delivery unit in the patient interface with a radiation beam delivery unit for delivering a radiation beams to tissue. All techniques and methods for FIG. 1 apply to the generalized radiation SP surgical system. The examples presented below are mostly based on pulsed laser surgical systems because laser tattoo removal and laser treatment of vascular malformation are major concerns of this invention.

Figure 2:
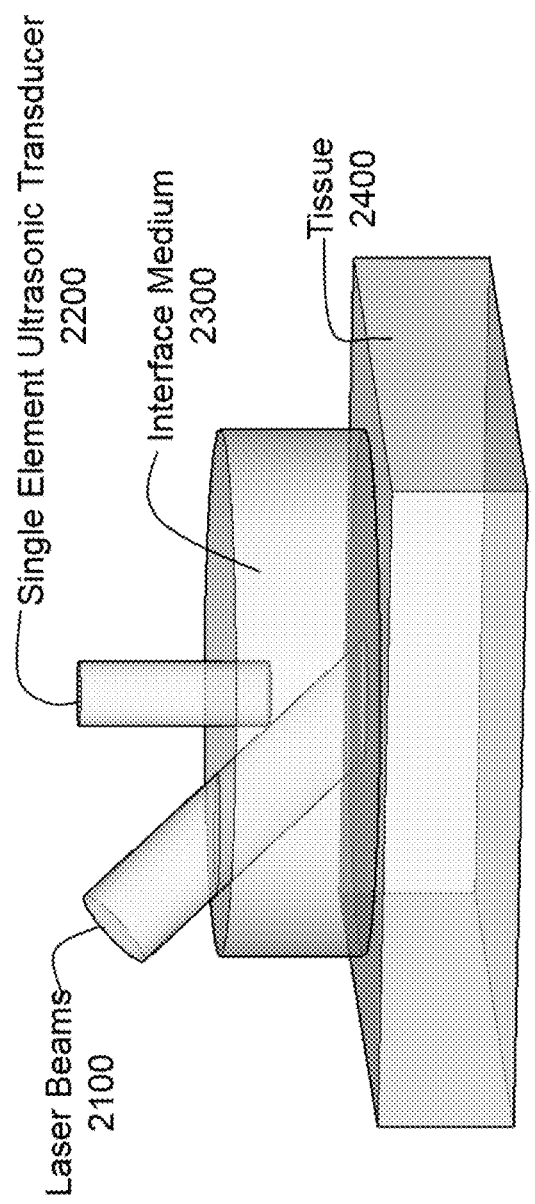
FIGS. 2-10 show examples of patient interfaces with different configurations to facilitate optimized selective photothermolysis with lasers.

FIGS. 2-10 show examples of patient interfaces with different configurations to facilitate optimized SP laser surgery. FIG. 2 shows a schematic example of a patient interface comprising a single element ultrasonic transducer 2200, and an interface medium 2300 in acoustic contact with tissue 2400. Because a light delivery unit that should be shown in the patient interface is no different from that of a conventional laser SP system, the light delivery unit is skipped in FIG. 2 for simplicity. Laser beams 2100 (a surgical laser beam, or a temperature-sensing laser beam, or both) can be selectively delivered to the tissue 2400 surface according to the requirements of the methods. In some implementations, laser beams 2100 could only comprise a surgical laser beam. The single element ultrasonic transducer 2200 is positioned to detect photoacoustic waves without blocking laser beams 2100. The transducer 2200 could be a traditional ultrasonic transducer or one based on optical detection techniques. The interface medium 2300 allows the transmission of laser beams and photoacoustic waves with minimum energy loss. The interface medium 2300 could be saved in a more simplified configuration where the single element ultrasonic transducer is in direct acoustic contact with tissue at a tissue surface area immediately next to a tissue surface area illuminated by the laser beams. One advantage of this simplified configuration is that it may simultaneously allow the delivery of skin cooling agent through free space. Spectroscopic photoacoustic signals are acquired by the single element ultrasonic transducer 2200 from a one-dimensional, depth-resolved space in the tissue, and are digitized and analyzed by the control system 1110 of FIG. 1.

Figure 3:
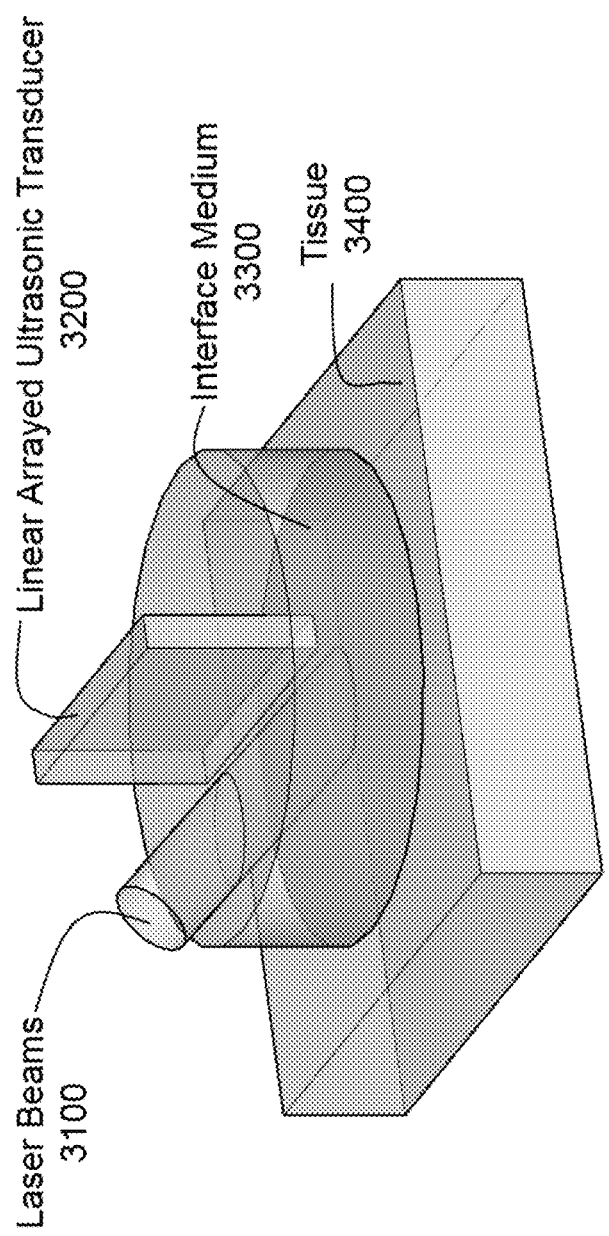

FIG. 3 shows another schematic example of a patient interface comprising a linear arrayed ultrasonic transducer 3200 and an interface medium 3300 in acoustic contact with tissue 3400. Because a light delivery unit that should be shown in the patient interface is no different from that of a conventional laser SP equipment, the light delivery unit is skipped in FIG. 3 for simplicity. Laser beams 3100 (a surgical laser beam, or a temperature-sensing laser beam, or both) can be selectively delivered to the tissue 3400 surface according to the requirements of the methods. The linear arrayed ultrasonic transducer 3200 is positioned to detect photoacoustic waves without blocking laser beams 3100. The linear arrayed transducer 3200 could be a traditional ultrasonic transducer or one based on optical detection techniques. The interface medium 3300 allows the transmission of laser beams and photoacoustic waves with minimum loss. The interface medium 3300 could also be saved in a more simplified configuration where the linear arrayed ultrasonic transducer is in direct acoustic contact with tissue at a tissue surface area immediately next to a tissue surface area illuminated by the laser beams delivered through free space. One advantage of this simplified configuration is that it may simultaneously allow the delivery of skin cooling agent through free space. Spectroscopic photoacoustic signals are acquired by the linear arrayed ultrasonic transducer 3200 from a two-dimensional, depth-resolved space in the tissue, and are digitized and analyzed by the control system 1110 shown in FIG. 1.

Figure 4:
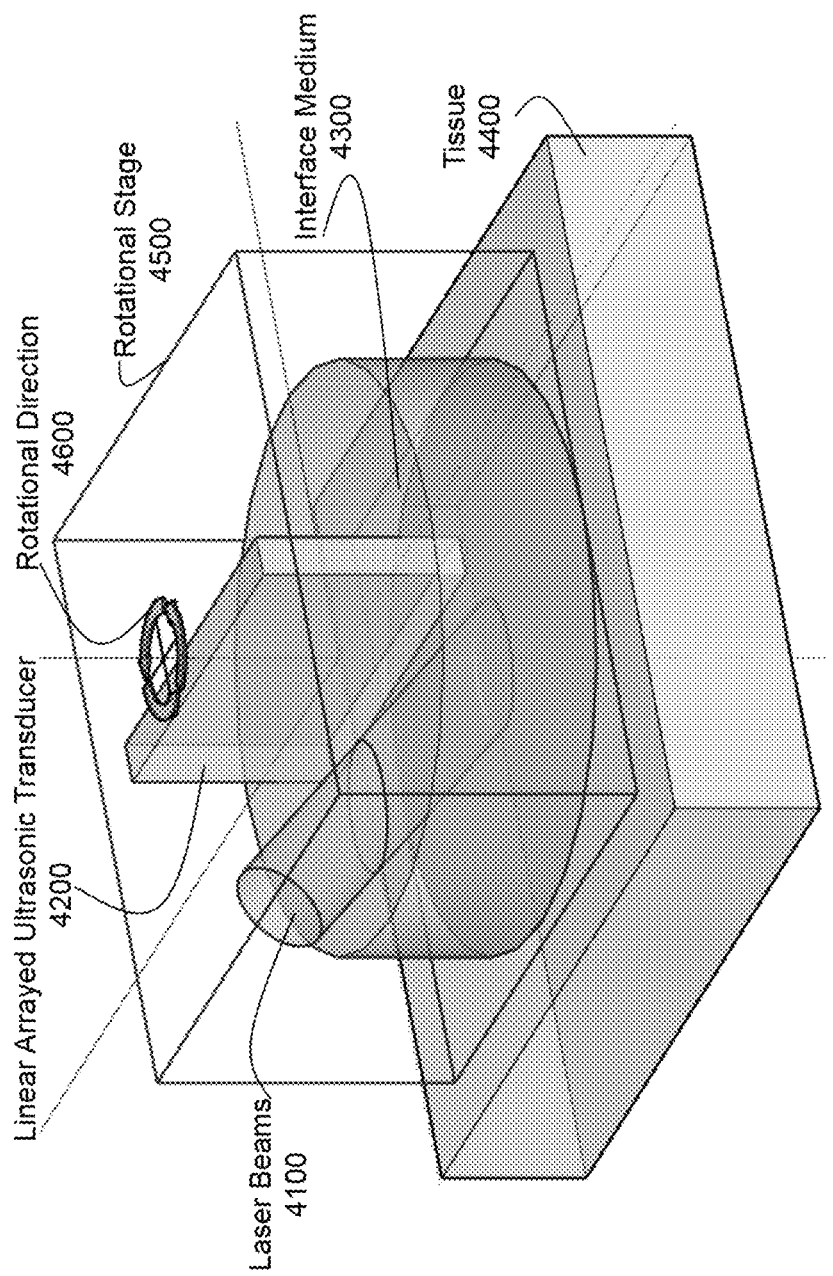

FIG. 4 shows another schematic example of a patient interface comprising a linear arrayed ultrasonic transducer 4200, an interface medium 4300 in acoustic contact with tissue 4400, and a rotational stage 4500 that mounts the linear arrayed ultrasonic transducer 4200 and the interface medium 4300 and rotates around the central axis of the illuminated oval area on tissue surface for the acquisition of a three-dimensional tissue information. The arrows 4600 show the rotational direction of the rotation stage 4500. Because a light delivery unit that should be shown in the patient interface is no different from that of a conventional laser SP system, the light delivery unit is skipped in FIG. 4 for simplicity. Laser beams 4100 (a surgical laser beam, or a temperature-sensing laser beam, or both) can be selectively delivered to the tissue 4400 surface according to the requirements of the methods. Laser beams 4100 are delivered with a flexible multimode fiber or a flexible fiber bundle and accessory optics (not shown in FIG. 4) to allow rotation. The linear arrayed ultrasonic transducer 4200 is positioned to detect photoacoustic waves without blocking laser beams 4100. The linear arrayed transducer 4200 could be a traditional ultrasonic transducer or one based on optical detection techniques. The interface medium 4300 allows the transmission of laser beams and photoacoustic waves with minimum loss. The interface medium 4300 could also be saved in a more simplified configuration where the linear arrayed ultrasonic transducer is in direct acoustic contact with tissue at a tissue surface immediately next to a tissue surface area illuminated by the laser beams delivered through free space. One advantage of this simplified configuration is that it may simultaneously allow the delivery of skin cooling agent through free space. Spectroscopic photoacoustic signals are acquired by the linear arrayed ultrasonic transducer 4200 from a three-dimensional, depth-resolved space in the tissue, and are digitized and analyzed by the control system 1110 shown in FIG. 1.

Figure 5:
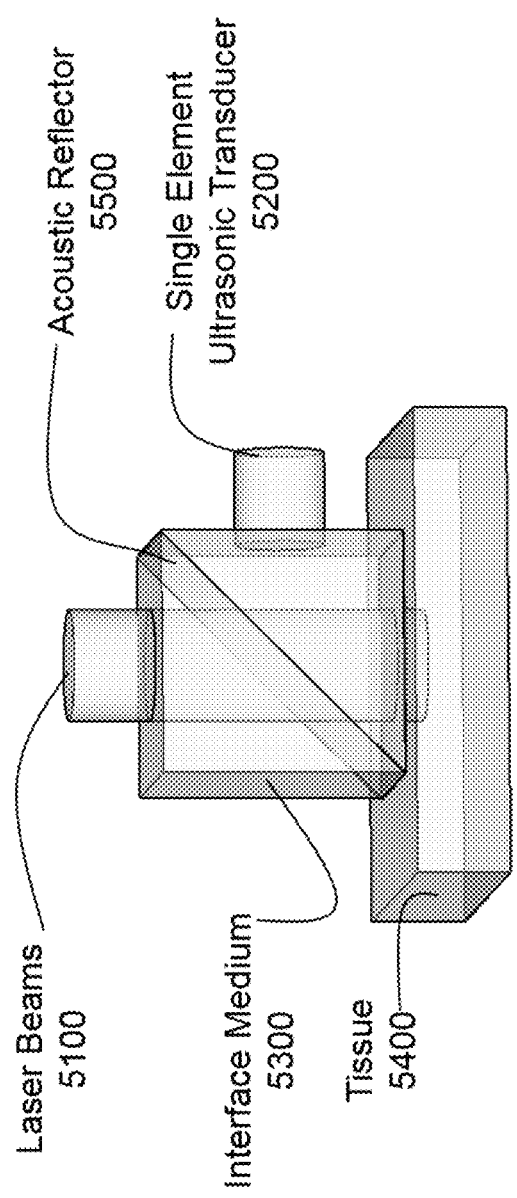

FIG. 5 shows another schematic example of a patient interface comprising a single element ultrasonic transducer 5200, an acoustic wave reflector 5500, and an interface media 5300 in acoustic contact with tissue 5400. Because a light delivery unit that should be shown in the patient interface is no different from that of a conventional laser SP system, the light delivery unit is skipped in FIG. 5 for simplicity. Laser beams 5100 (a surgical laser beam, or a temperature-sensing laser beam, or both) can be selectively delivered to the tissue 5400 surface according to the requirements of the methods. The single element ultrasonic transducer 5200 is positioned to detect photoacoustic waves reflected by the acoustic reflector 5500 without blocking laser beams 5100. The usage of an acoustic reflector 5500 allows the laser beams and the transducer on the same side of tissue without blocking each other. The single element ultrasonic transducer 5200 could be a traditional ultrasonic transducer or one based on optical detection techniques. The interface medium 5300 allows the transmission of laser beams and photoacoustic waves with minimum loss. Spectroscopic photoacoustic signals are acquired by the single element ultrasonic transducer 5200 from a one-dimensional, depth-resolved space in the tissue, and are digitized and analyzed by the control system 1110 shown in FIG. 1.

Figure 6:
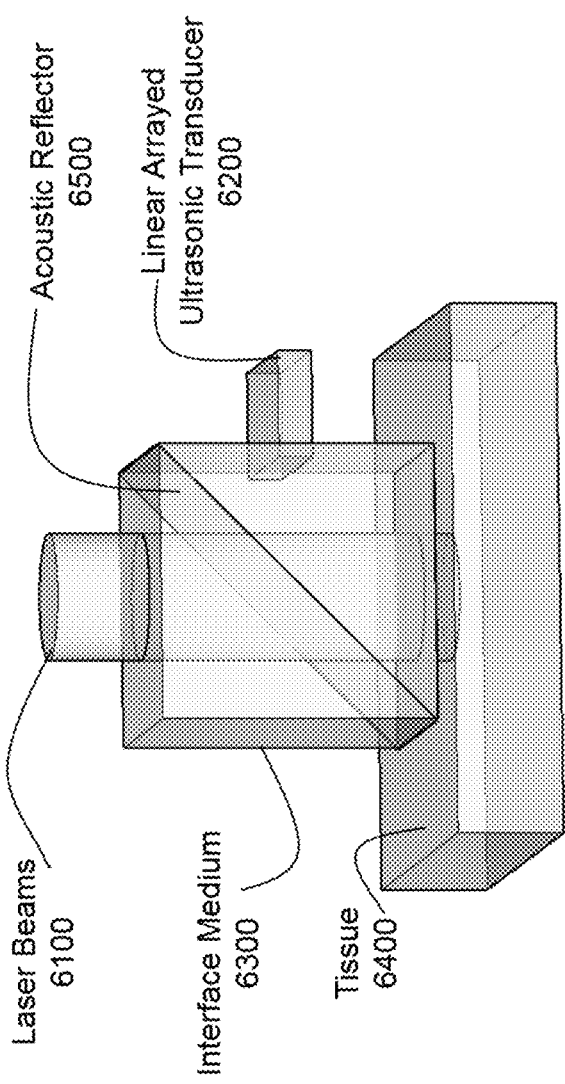

FIG. 6 shows another schematic example of a patient interface comprising a linear arrayed ultrasonic transducer 6200, an acoustic reflector 6500, and an interface media 6300 in acoustic contact with tissue 6400. Because a light delivery unit that should be shown in the patient interface is no different from that of a conventional laser SP system, the light delivery unit is skipped in FIG. 6 for simplicity. Laser beams 6100 (a surgical laser beam, or a temperature-sensing laser beam, or both) can be selectively delivered to the tissue 6400 surface according to the requirements of the methods. The linear arrayed ultrasonic transducer 6200 is positioned to detect photoacoustic waves reflected by the acoustic reflector 6500. The usage of an acoustic reflector 6500 allows the laser beams and the transducer on the same side of tissue without blocking each other. The linear arrayed ultrasonic transducer 6200 could be a traditional ultrasonic transducer or one based on optical detection techniques. The interface medium 6300 allows the transmission of laser beams and photoacoustic waves with minimum loss. Spectroscopic photoacoustic signals are acquired by the linear arrayed ultrasonic transducer 6200 from a two-dimensional, depth-resolved space in the tissue, and are digitized and analyzed by the control system 1110 shown in FIG. 1.

Figure 7:
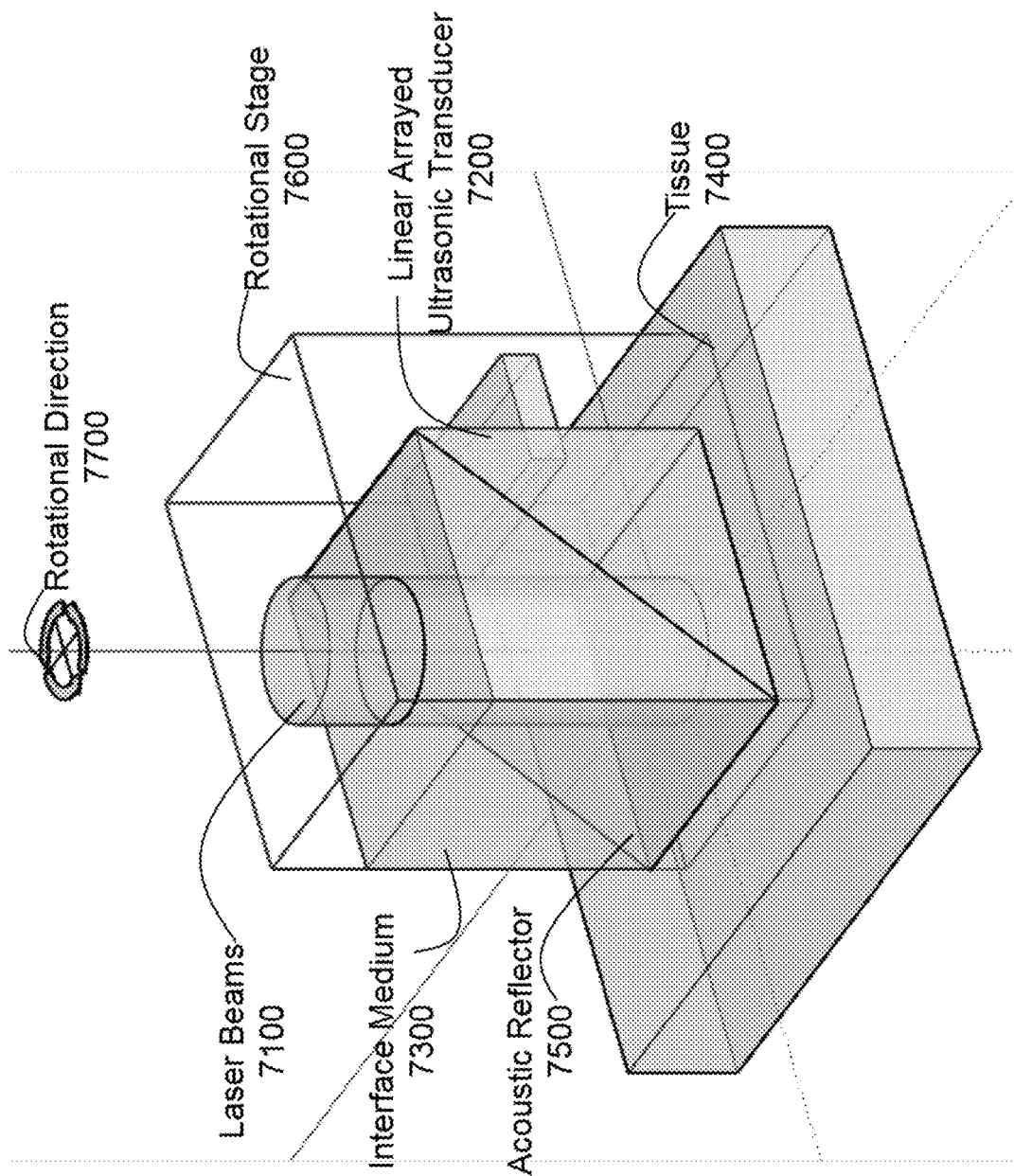

FIG. 7 shows another schematic example of a patient interface comprising a linear arrayed ultrasonic transducer 7200, an acoustic reflector 7500, an interface media 7300 in acoustic contact with tissue 7400, and a rotational stage 7600 that mounts the linear arrayed ultrasonic transducer 7200, the acoustic reflector 7500 and the interface medium 7300, and rotates around the axis of the laser beams. The arrows 7700 show the rotational direction of the rotation stage 7600. Because a light delivery unit that should be shown in the patient interface is no different from that of a conventional laser SP system, the light delivery unit is skipped in FIG. 7 for simplicity. Laser beams 7100 (a surgical laser beam, or a temperature-sensing laser beam, or both) can be selectively delivered to the tissue 7400 surface according to the requirements of the methods. The linear arrayed ultrasonic transducer 7200 is positioned to detect photoacoustic waves reflected by the acoustic reflector 7500. The usage of acoustic reflector 7500 allows the laser beams and the transducer on the same side of tissue without blocking each other. The linear arrayed ultrasonic transducer 7200 could be a traditional ultrasonic transducer or one based on optical detection techniques. The interface medium 7300 allows the transmission of laser beams and photoacoustic waves with minimum loss. Spectroscopic photoacoustic signals are acquired by the linear arrayed ultrasonic transducer 7200 from a three-dimensional, depth-resolved space in the tissue, and are digitized and analyzed by the control system 1110 shown in FIG. 1.

Figure 8:
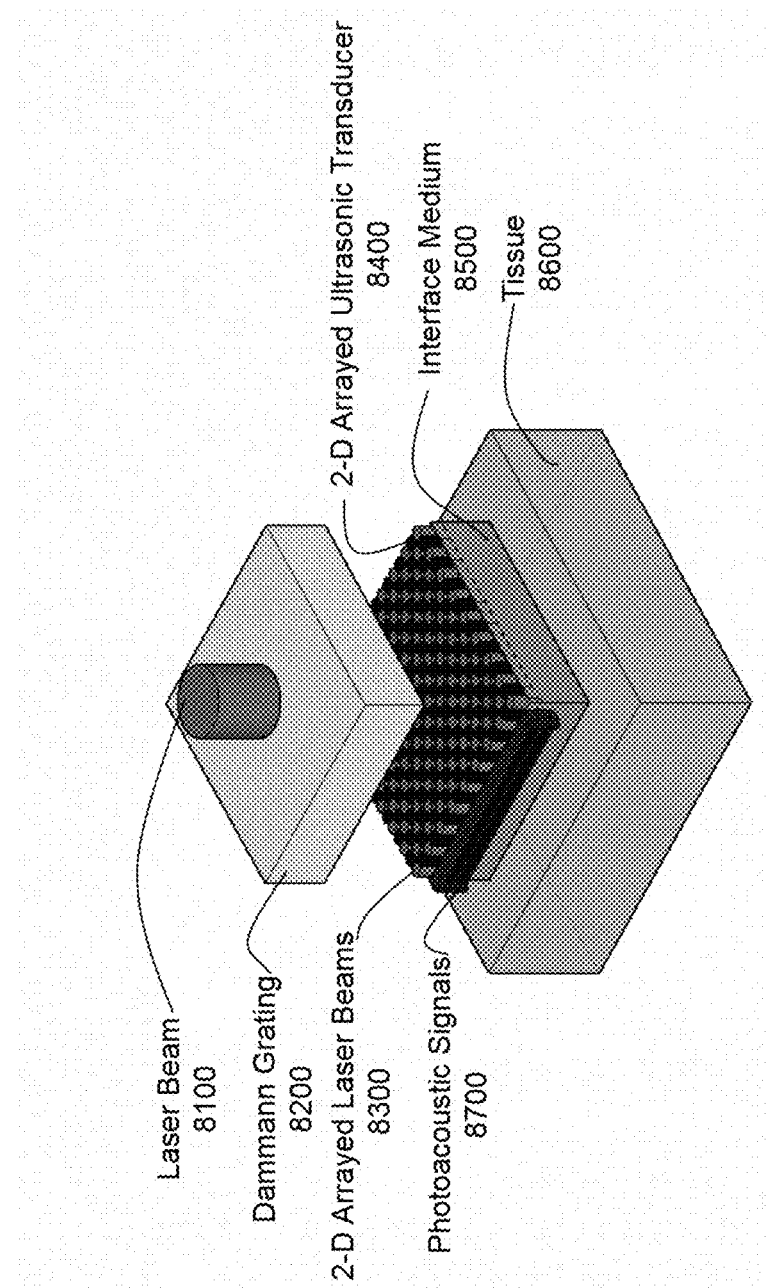

FIG. 8 shows another schematic example of a patient interface comprising a Dammann grating 8200, a 2-D arrayed ultrasonic transducer 8400, and an interface medium 8500 in acoustic contact with tissue 8600. Because a light delivery unit that should be shown in the patient interface is no different from that of a conventional laser SP system, the light delivery unit is skipped in FIG. 8 for simplicity. Laser beams 8100 (a surgical laser beam, or a temperature-sensing laser beam, or both) can be selectively delivered to the tissue 8600 surface according to the requirements of the methods. The laser beams are transformed into 2-D arrayed laser beams 8300 by a Dammann grating 8200. 2-D arrayed laser beams pass through the free space not being taken by the 2-D arrayed ultrasonic transducer 8400 and the interface medium 8500 before reaching the tissue 8600. The excited photoacoustic waves are detected by the 2-D arrayed ultrasonic transducer 8400. The 2-D arrayed ultrasonic transducer 8400 could be a traditional ultrasonic transducer or one based on optical detection techniques. The interface medium 7300 allows the transmission of laser beams and photoacoustic waves with minimum loss. Spectroscopic photoacoustic signals 8700 are acquired by the 2-D arrayed ultrasonic transducer 8400 from a three-dimensional, depth-resolved space in the tissue, and are digitized and analyzed by the control system 1110 shown in FIG. 1.

Figure 9:
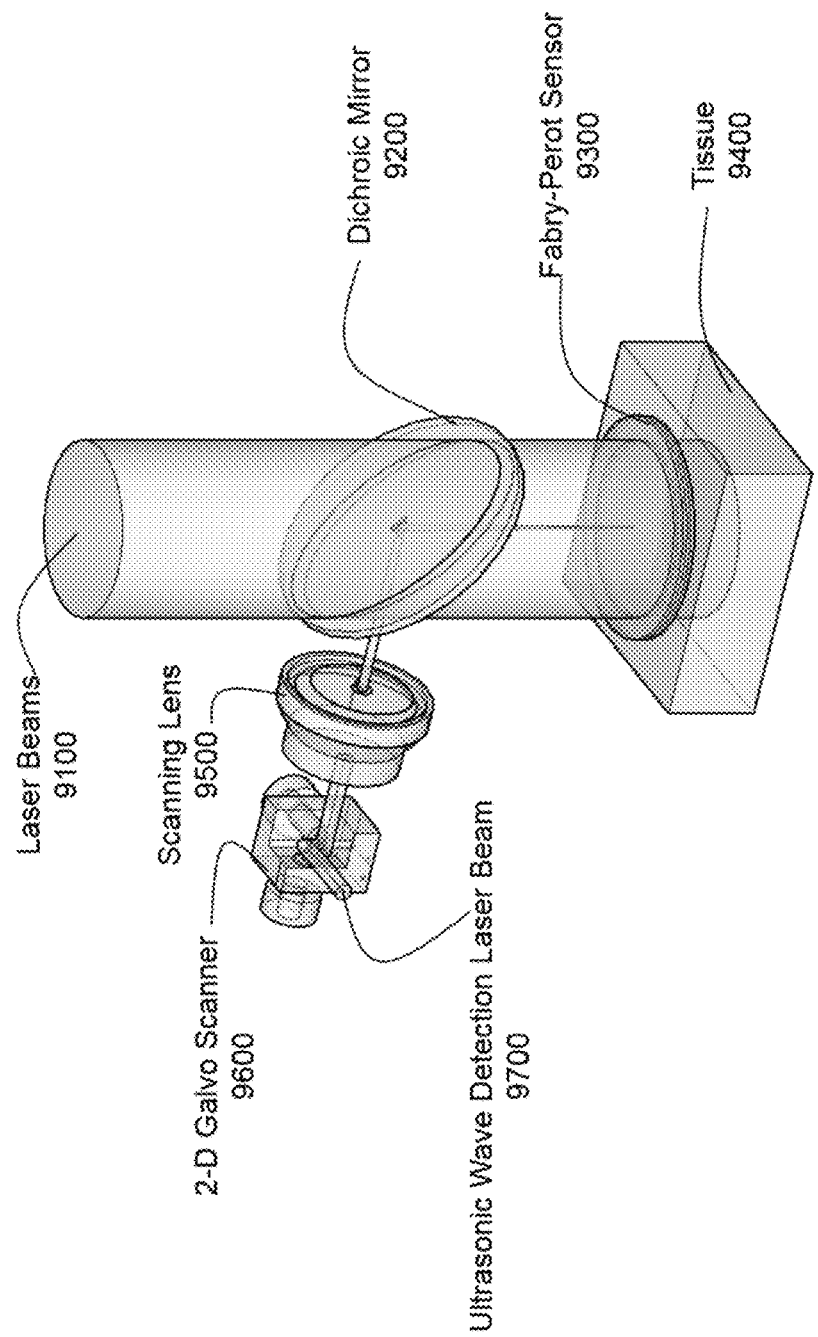

FIG. 9 shows another schematic example of a patient interface comprising a dichroic mirror 9200, a scanning lens 9500, a 2-D Galvo scanner 9600, and a Fabry-Perot sensor 9300 in acoustic contact with a tissue 9400. Because a light delivery unit that should be shown in the patient interface is no different from that of a conventional laser SP system, the light delivery unit is skipped in FIG. 9 for simplicity. Laser beams 9100 (a surgical laser beam, or a temperature-sensing laser beam, or both) can be selectively delivered to the tissue 9400 surface according to the requirements of the methods. Both the dichroic mirror 9200 and the Fabry-Perot sensor 9300 are transparent for the laser beams 9100 (a surgical laser beam, or a temperature-sensing laser beam, or both). An ultrasonic-wave-detection laser beam 9700 is scanned by the 2-D Galvo scanner 9600 and the scanning lens 9500, and reflected by the dichroic mirror 9200 to the Fabry-Perot sensor 9300 for the detection of photoacoustic waves. The Fabry-Perot sensor 9300 comprises of two layers of dielectric mirrors and an acoustic-wave-sensing layer between two dielectric mirrors. The ultrasonic-wave-detection laser beam 9700 could be in the form of 1-D arrayed laser beams or 2-D arrayed laser beams in other implementations. An optical system that sends out the ultrasonic-wave-detection laser beam 9700, detects the reflected ultrasonic-wave-detection laser beam 9700 modulated by photoacoustic waves is skipped from FIG. 9 for simplicity. Spectroscopic photoacoustic signals could be acquired from a one-dimensional or a two-dimensional or a three-dimensional, depth-resolved space in the tissue, and be digitized and analyzed by the control system 1110 shown in FIG. 1.

Figure 10:
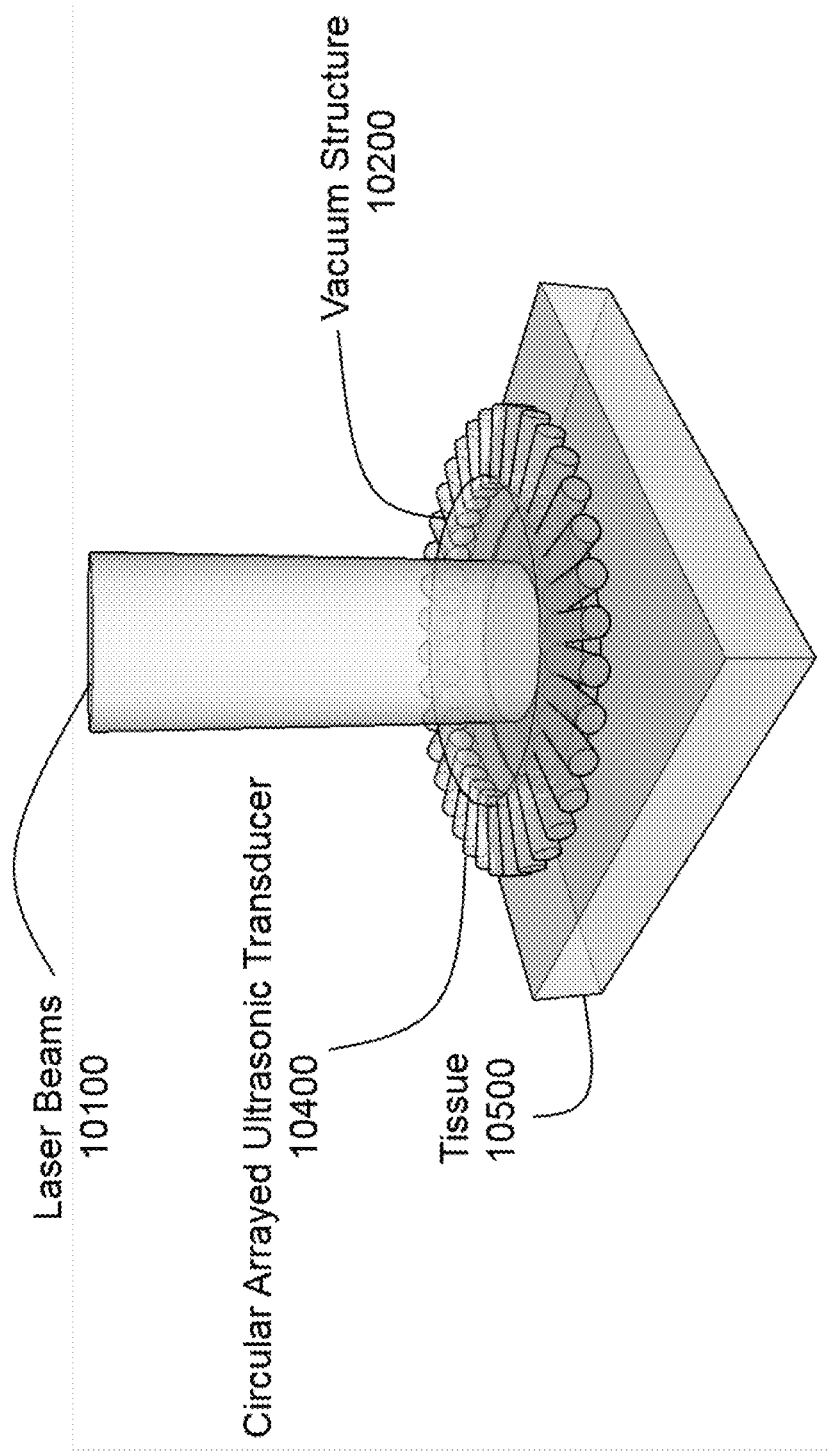

FIG. 10 shows another schematic example of a patient interface comprising a vacuum structure 10200, a circular arrayed ultrasonic transducer 10400, and an interface medium 10300 in acoustic contact with a tissue 10500. Because a light delivery unit that should be shown in the patient interface is no different from that of a conventional laser SP system, the light delivery unit is skipped in FIG. 10 for simplicity. Laser beams 10100 (a surgical laser beam, or a temperature-sensing laser beam, or both) can be selectively delivered to the tissue 10500 surface according to the requirements of the methods. The circular arrayed transducer 10400 could be a traditional ultrasonic transducer or one based on optical detection techniques. The circular arrayed ultrasonic transducer 10400 is in acoustic contact with the wall of the vacuum structure 10200. The vacuum structure 10200 is designed to suck part of the tissue into it in a way similar to a body cupping device. Interface medium 10300 such as water could be injected into the bottom of the vacuum structure to immerse the tissue sucked into the vacuum structure. The laser beams 10100 illuminate the tissue inside of the vacuum structure and excite photoacoustic waves. The circular arrayed ultrasonic transducer 10400 could acquire spectroscopic photoacoustic signals from a two-dimensional, depth-resolved space in the tissue. The circular arrayed ultrasonic transducer 10400 could be adjusted in elevational direction for acquiring spectroscopic photoacoustic signals from a three-dimensional, depth-resolved space in the tissue. The spectroscopic photoacoustic signals are digitized and analyzed by the control system 1110 shown in FIG. 1.

Figure 11:
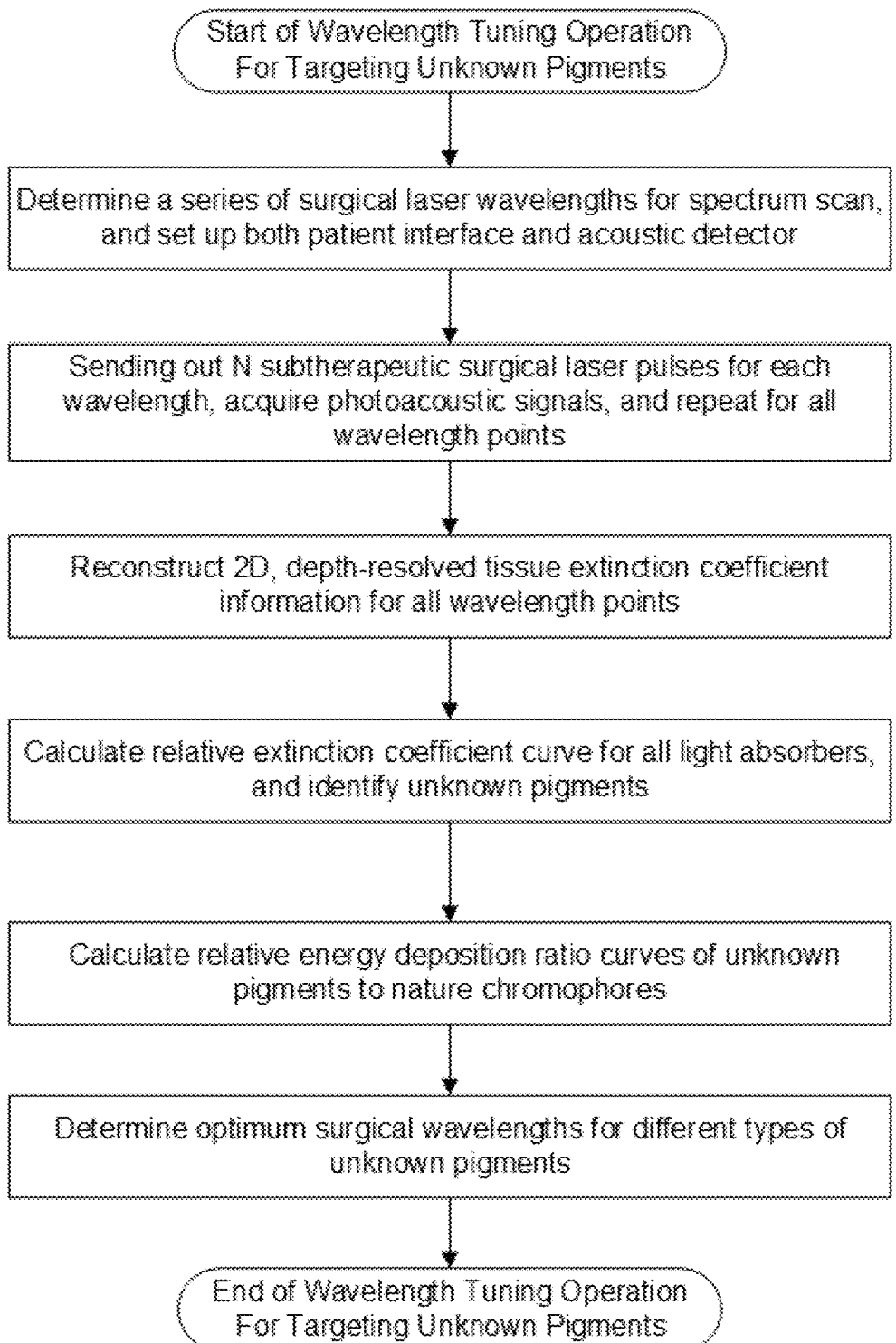
FIG. 11 shows an example of wavelength tuning operation for optimizing selective photothermolysis of unknown pigments.

FIG. 11 shows an example of wavelength tuning operation for optimizing SP laser treatment of unknown pigments. The optimal surgical laser wavelength should maximize the laser energy deposition ratios of unknown pigments to nature chromophores. The following procedure is designed for a laser SP surgery system whose surgical laser pulse width is short enough to effectively excite photoacoustic signals. However, if the surgical laser pulse is too long to effectively excite photoacoustic signals, a short temperature-sensing laser pulse generated by a more advanced dual-pulse (a surgical laser pulse followed by a delayed temperature-sensing laser pulse) laser system should be used to excite photoacoustic signals in the following procedure. First, a series of wavelength points that comprises characteristic peaks and valleys of oxygenated hemoglobin and deoxygenated hemoglobin is determined; Second, a tissue area is selected and the patient interface is operated to be in acoustic contact with the selected tissue area; Third, the acoustic detector is preferably configured in the mode of acquiring a 2-D, depth-resolved photoacoustic tissue information with a single surgical laser pulse. It is noted that the acoustic detector could be configured to acquire 1-D, depth-resolved tissue information in a simplified implementation and the following steps might need slight modifications; Fourth, the control system sends out multiple subtherapeutic surgical laser pulses for each wavelength point, and acquires photoacoustic signals detected by the acoustic detector; Fifth, an averaged 2-D, depth-resolved tissue information is acquired after tomography reconstruction for each wavelength point; Sixth, unknown pigments are identified along with nature chromophores after their relative extinction coefficients are calculated and their relative extinction coefficient curves are fitted. If no nature chromophores are presented in the 2-D, depth-resolved tissue space, known extinction coefficient curves of nature chromophores from literature could be used; Seventh, relative energy deposition ratio curves of unknown pigments to nature chromophores are calculated; Finally, the optimal surgical laser wavelengths are determined for different types of unknown pigments with an algorithm that puts different priority weights on different nature chromophores. Multiple laser treatments with optimized lasing wavelengths for different types of unknown pigments might be performed in series for the optimal laser treatment outcome. The same technique in FIG. 11 applies to pulsed laser (coherent light source) SP surgical systems, other non-coherent pulsed light-source SP surgical systems where the central wavelength of the non-coherent pulsed light source is tuned, and other general radiation SP systems using a wavelength-tunable, pulsed or modulated radiation beam to effectively excite photoacoustic waves from lesions in tissue or extraneous contrast agents attached to lesions in tissue.

For the more advanced dual-pulse (a surgical laser pulse followed by a delayed temperature-sensing laser pulse) laser SP surgical system, this invention provides a method for photoacoustic temperature sensing in live tissue including a non-invasive Grüneisen parameter calibration procedure. This method overcome limitations of methods in prior art. This method detailed in FIGS. 12 and 13 can non-invasively measure dynamic temperature of a surgical target in a tissue heated by a short surgical laser pulse after calibration. The calibration procedure is based on a hypothesis that the heating of a surgical target by laser pulses is a linear process and the maximum temperature rise of the surgical target is proportional to the laser energy deposited into the surgical target when the temperature is measured immediately after the surgical laser pulse.

Figure 12:
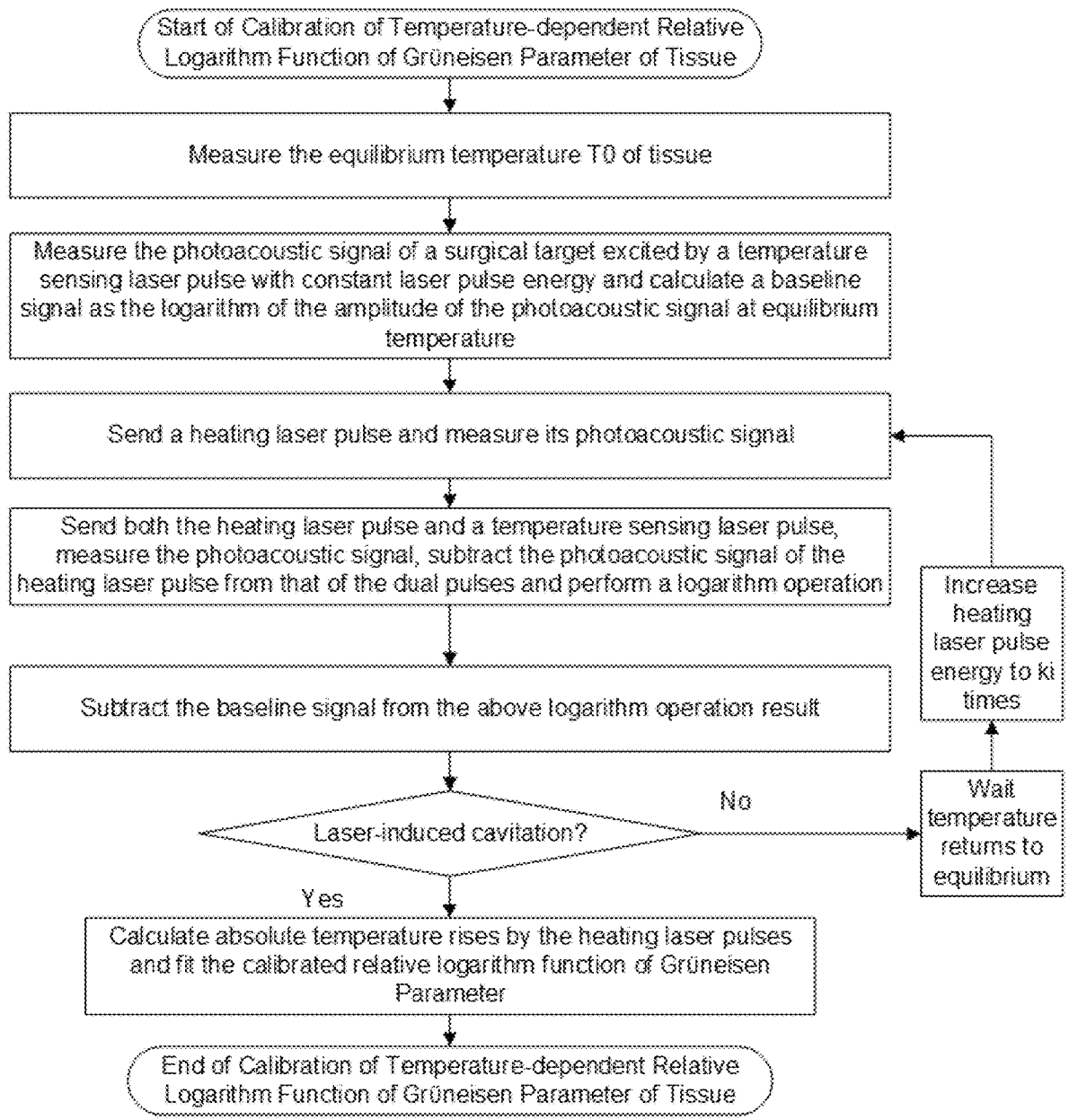
FIG. 12 shows an example of calibrating a temperature-dependent relative logarithm function of Grüneisen parameter of a tissue.

FIG. 12 shows an example of calibrating a temperature-dependent relative logarithm function of Grüneisen parameter of tissue. First, we start calibration process by measuring the equilibrium temperature T0 of the tissue; Second, we measure the photoacoustic signal of a surgical target excited by a temperature-sensing laser pulse with a constant laser pulse energy, perform a logarithm operation on the photoacoustic signal amplitude, and get a baseline signal; Third, we send a surgical laser pulse for heating the surgical target and measure the photoacoustic signal excited by the surgical laser pulse; Fourth, we send both the surgical laser pulse and the temperature-sensing laser pulse, measure the excited photoacoustic signal by dual pulses, subtract the photoacoustic signal excited by the surgical laser pulse from that of the dual pulses, calculate the amplitude of the photoacoustic signal excited by the temperature-sensing laser pulse, separate temperature-dependent part from other temperature-independent parts with a logarithm operation, subtract the baseline signal, and calculate a relative logarithm function value, $\log\Gamma(T0+\delta T)-\log\Gamma(T0)$ where $\Gamma$ denotes the Grüneisen parameter of the tissue and $\delta T$ denotes the temperature rise caused by the heating laser pulse, for the temperature point of $T0+\delta T$; Fifth, if the recorded photoacoustic signal amplitude does not show an abrupt increase due to the laser-induced cavitation at 100° C., we wait until the tissue temperature returns to its original equilibrium temperature. Then we adjust the heating laser pulse energy to its ki times and return to the third step for acquiring another relative logarithm function value of $\log\Gamma(T0+ki\delta T)-\log\Gamma(T0)$ for the temperature point of $T0+ki\delta T$. We should keep the increase of the surgical laser energy small in order to have a more accurate measurement of 100° C. If a laser-induced cavitation is observed, we continue to the final step. In the final step, we have $$T0+k0\delta T<T0+k1\delta T<T0+k2\delta T<\ldots<T0+km\delta T=100°\text{ C.}$$

Thus, we can calculate the absolute temperature rises (k0δT, k1δT, kmδT) by each surgical laser pulse and fit the function of $\log\Gamma(T)-\log\Gamma(T0)$ between T0 and 100° C. where T denotes temperature. The equilibrium temperature could be the body temperature of a patient. It could also be an equilibrium temperature of an ex vivo tissue in an environment of known temperature. In practice, laser pulse energy fluctuates from pulse to pulse. Compensation with simultaneous laser pulse energy monitoring is necessary for the procedures above. As long as both the starting temperature and the temperature to be measured are between T0 and 100° C., the calibrated relative logarithm function Grüneisen parameter of tissue is valid for a temperature sensing operation as detailed below.

Figure 13:
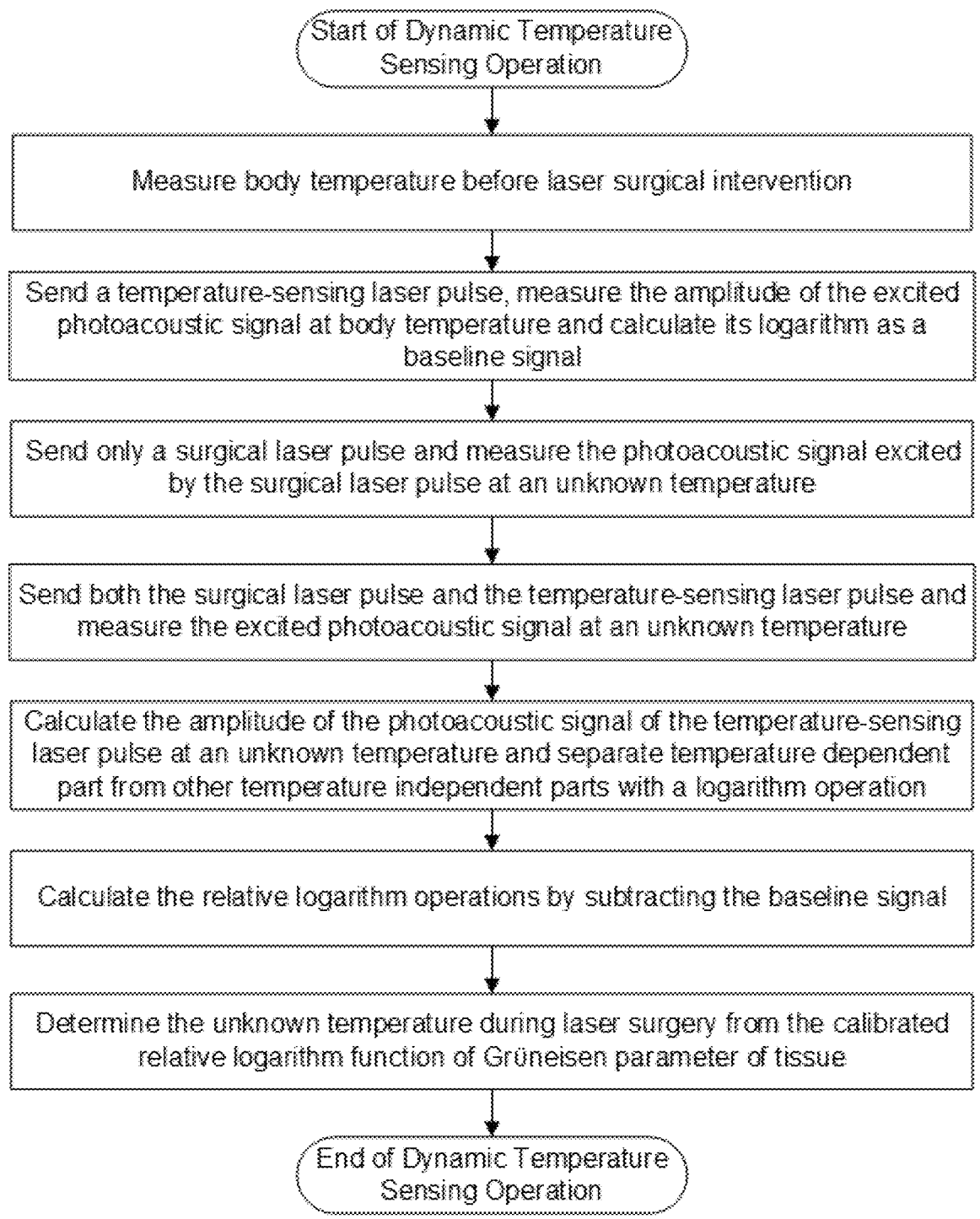
FIG. 13 shows an example of dynamic temperature-sensing operation of a surgical target in a tissue after heating by a short surgical laser pulse.

FIG. 13 shows an example of dynamic temperature sensing operation of surgical targets in a tissue after heating by a short surgical laser pulse. However, if the delay time between the surgical laser pulse and the temperature-sensing laser pulse is adjusted, the dynamic temperature variation profile of a surgical target along time can be accurately measured by repeating the following dynamic temperature sensing procedure. It is important that we start from a known body temperature and we know the starting point in the relative logarithm function of Grüneisen parameter. First, we measure body temperature before laser surgical intervention; Second, we send a temperature-sensing laser pulse, measure the amplitude of the excited photoacoustic signal at body temperature and calculate its logarithm as a baseline signal; Third, we send only a surgical laser pulse and measure the photoacoustic signal excited by the surgical laser pulse; Fourth, we send both the surgical laser pulse and the temperature-sensing laser pulse and measure the excited photoacoustic signal; Fifth, we calculate the amplitude of the photoacoustic signal excited by the temperature-sensing laser pulse and separate temperature-dependent part from other temperature-independent parts with a logarithm operation; Sixth, we calculate the relative logarithm function value by subtracting the baseline signal; Finally, we determine the dynamic temperature at the end of the surgical laser pulse from the calibrated relative logarithm function of Grüneisen parameter of tissue. For temperature sensing of a surgical target heated by a continuous-wave laser, it requires only two measurements of the photoacoustic signals excited by the temperature-sensing laser pulse at the body temperature and at a time point during CW laser surgery. More accurate measurement result is expected due to the more accurate, non-invasive calibration method in FIG. 12. The same technique in FIGS. 12-13 applies to pulsed laser (coherent light source) surgical systems, other non-coherent pulsed light-source surgical systems, high-intensity-focused-ultrasound therapy systems, and other general radiation SP systems using a surgical pulsed radiation beam to heat up lesions in tissue or extraneous contrast agents attached to lesions in tissue, and a pulsed or modulated temperature-sensing radiation beam to effectively excite photoacoustic waves from lesions in tissue or extraneous contrast agents attached to lesions in tissue.

Figure 14:
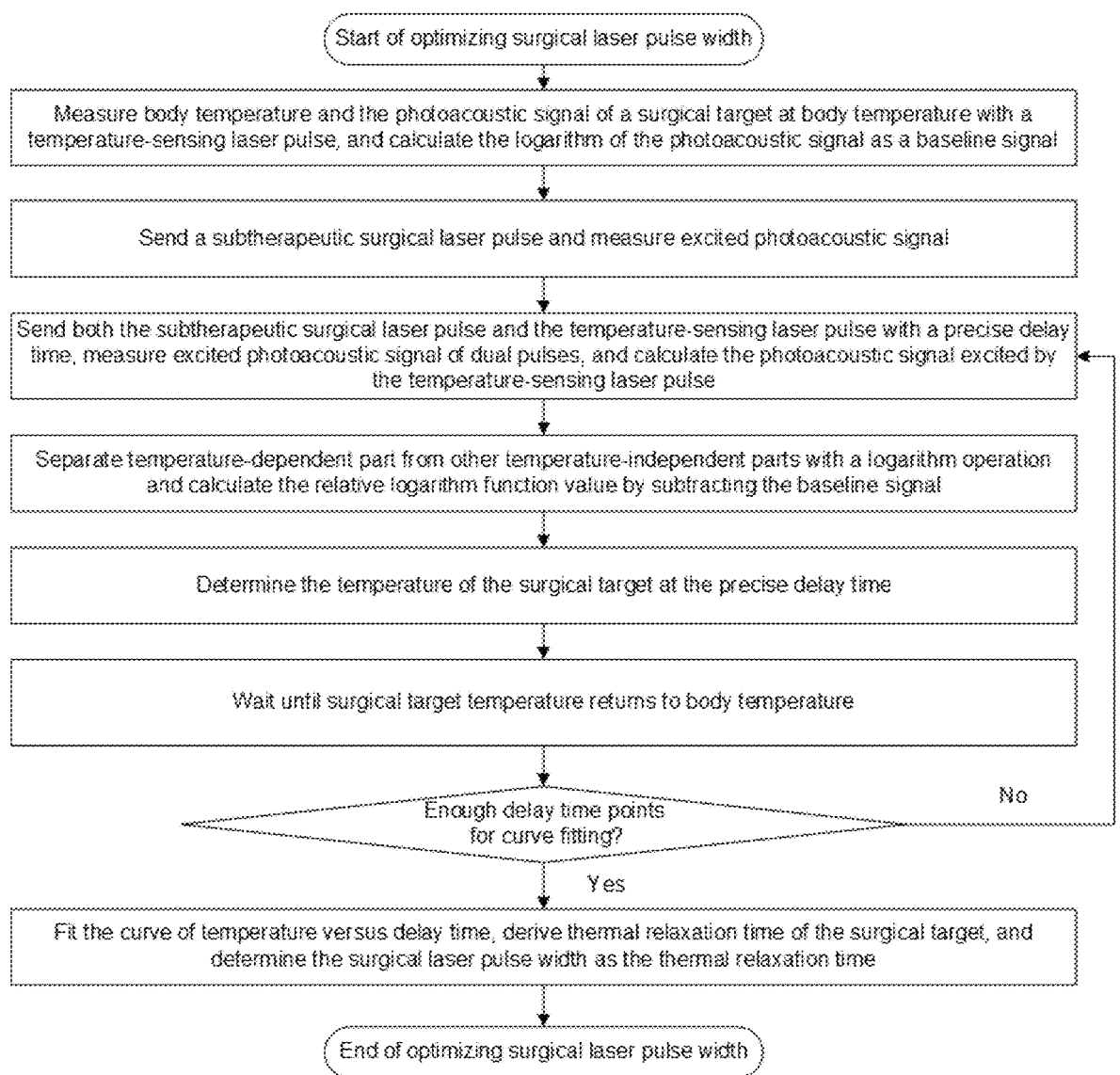
FIG. 14 shows an example of optimizing surgical laser pulse width by in vivo measuring thermal relaxation time of a surgical target in a tissue.

In applications such as laser treatment of vascular malformations, it is desirable to effectively heat a surgical target with laser pulses whose laser pulse width matches to thermal relaxation time of the surgical target. Most energy of laser pulse will be confined to the surgical target instead of being spread to surrounding healthy tissues. Computer simulation with tissue models and a surgical target's dimension information is the only available method to estimate thermal relaxation time of a surgical target in tissue in the research field of laser treatment of vascular malformation. However, FIG. 14 shows an example of optimizing surgical laser pulse width by in vivo measurement of thermal relaxation time of a surgical target in tissue. In addition to the surgical laser pulse, a temperature-sensing laser pulse is required to perform the task of measuring thermal relaxation time of a surgical target. First, we measure body temperature and the photoacoustic signal of a surgical target at body temperature with a temperature-sensing laser pulse, and calculate the logarithm of the photoacoustic signal as a baseline signal; Second, we send a subtherapeutic surgical laser pulse and measure excited photoacoustic signal; Third, we send both the subtherapeutic surgical laser pulse and the temperature-sensing laser pulse with a precise delay time, measure excited photoacoustic signal of dual pulses, and calculate the amplitude of the photoacoustic signal excited by the temperature-sensing laser pulse; Fourth, we separate temperature-dependent part from other temperature-independent parts with a logarithm operation and calculate the relative logarithm function value by subtracting the baseline signal; Fifth, we determine the temperature of the surgical target at the precise delay time; Sixth, we wait until surgical target temperature returns to body temperature, and determine whether there are enough delay time points to fit the curve of the surgical target's temperature versus delay time. If there are no enough delay time points, we change the value of the delay time and repeat the procedures between the third step and the sixth step before we can fit the curve of temperature versus delay time and derive the thermal relaxation time of the surgical target. The optimal surgical laser pulse width is determined to be equal to the measured thermal relaxation time of the surgical target. The same technique in FIG. 14 applies to pulsed laser (coherent light source) SP surgical systems, other non-coherent pulsed light-source SP surgical systems, and other general radiation SP systems using a surgical pulsed radiation beam to heat up lesions in tissue or extraneous contrast agents attached to lesions in tissue, and a pulsed or modulated temperature-sensing radiation beam to effectively excite photoacoustic waves from lesions in tissue or extraneous contrast agents attached to lesions in tissue.

In a conventional laser SP surgery, surgical laser pulse energy is selected according to a clinician's past experiences. However, the inclusion of an acoustic detector makes it possible to optimize surgical laser pulse energy objectively for the first time. For the laser treatment vascular malformations, the optimal laser pulse energy would heat the selected surgical target to a predetermined temperature for photocoagulation. For applications based on laser photodisruption such as laser tattoo removal, the optimal surgical laser pulse energy would heat a selected surgical target to 100° C. and cause laser-induced cavitation.

Figure 15:
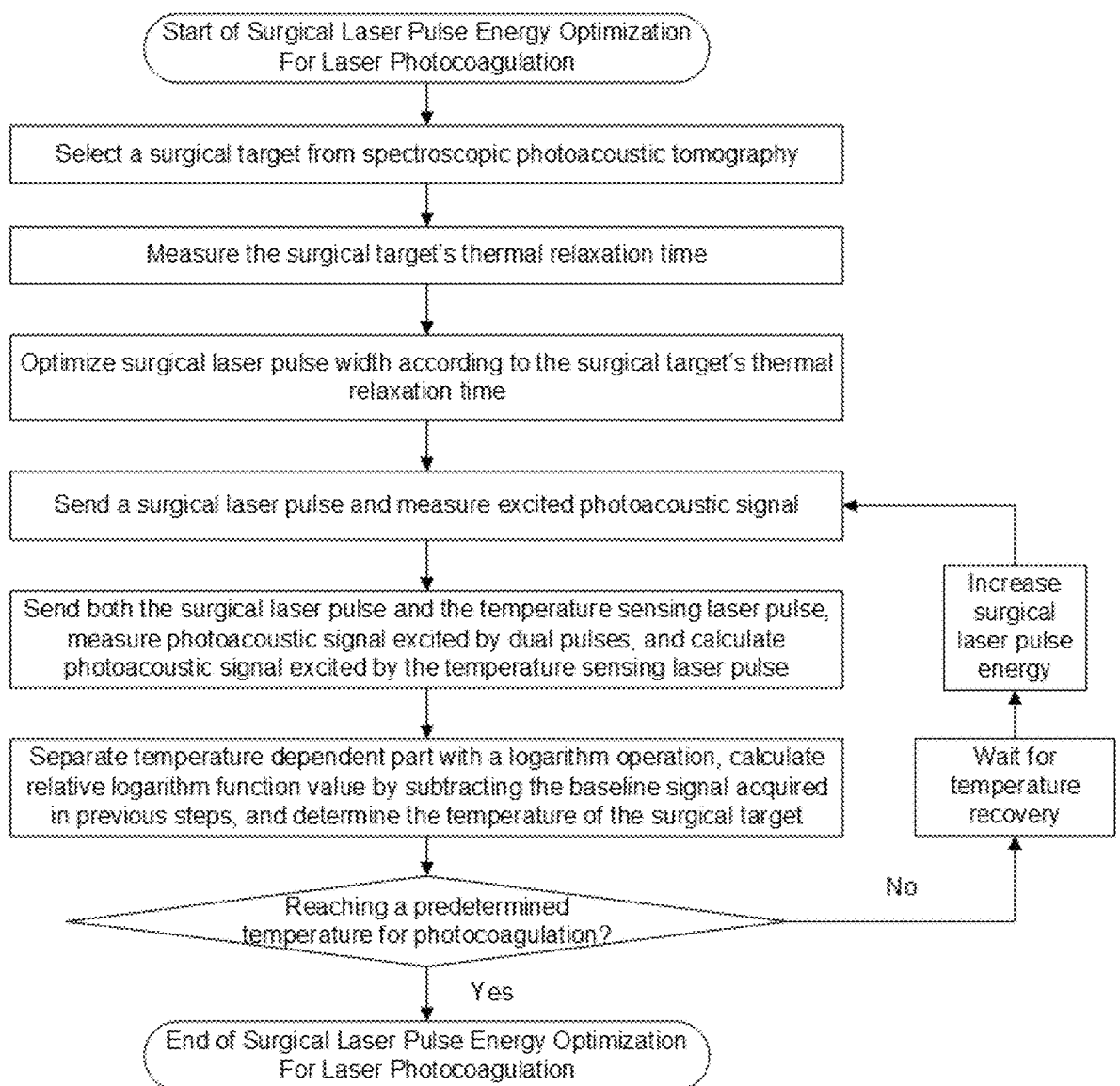
FIG. 15 shows an example of in vivo surgical laser pulse energy optimization for laser photocoagulation during a laser surgery.

FIG. 15 shows an example of surgical laser pulse energy optimization in a tunable laser during a laser photocoagulation SP surgery. We assume the laser wavelength is already optimized before laser power optimization. First, we select a surgical target with a 2-D, depth resolved tissue information excited by a temperature-sensing laser pulse and acquired by an acoustic detector; Second, we optimize laser pulse width after measuring the surgical target's thermal relaxation time; Third, we send a surgical laser pulse and measure excited photoacoustic signal; Fourth, we send both the surgical laser pulse and the temperature-sensing laser pulse, measure the photoacoustic signal excited by dual pulses, and calculate the amplitude of the photoacoustic signal excited by the temperature-sensing laser pulse; Fifth, we separate the temperature-dependent part with a logarithm operation, calculate a relative logarithm function value by subtracting the baseline signal acquired in previous steps, and determine the temperature of the surgical target; Sixth, we determine whether the surgical target reaches a predetermined temperature for photocoagulation. If not, we wait for the temperature to recover its original body temperature, increase the laser pulse energy and return to the third step. If the temperature reaches to a predetermined temperature for photocoagulation, we end the operation with the optimized laser pulse energy for photocoagulation of the surgical target. The same technique in FIG. 15 applies to pulsed laser (coherent light source) SP surgical systems, other non-coherent pulsed light-source SP surgical systems, high-intensity-focused-ultrasound therapy systems for optimizing ultrasound beam energy, and other general radiation SP systems using a surgical pulsed radiation beam to heat up lesions in tissue or extraneous contrast agents attached to lesions in tissue, and a pulsed or modulated temperature-sensing radiation beam to effectively excite photoacoustic waves from lesions in tissue or extraneous contrast agents attached to lesions in tissue.

Figure 16:
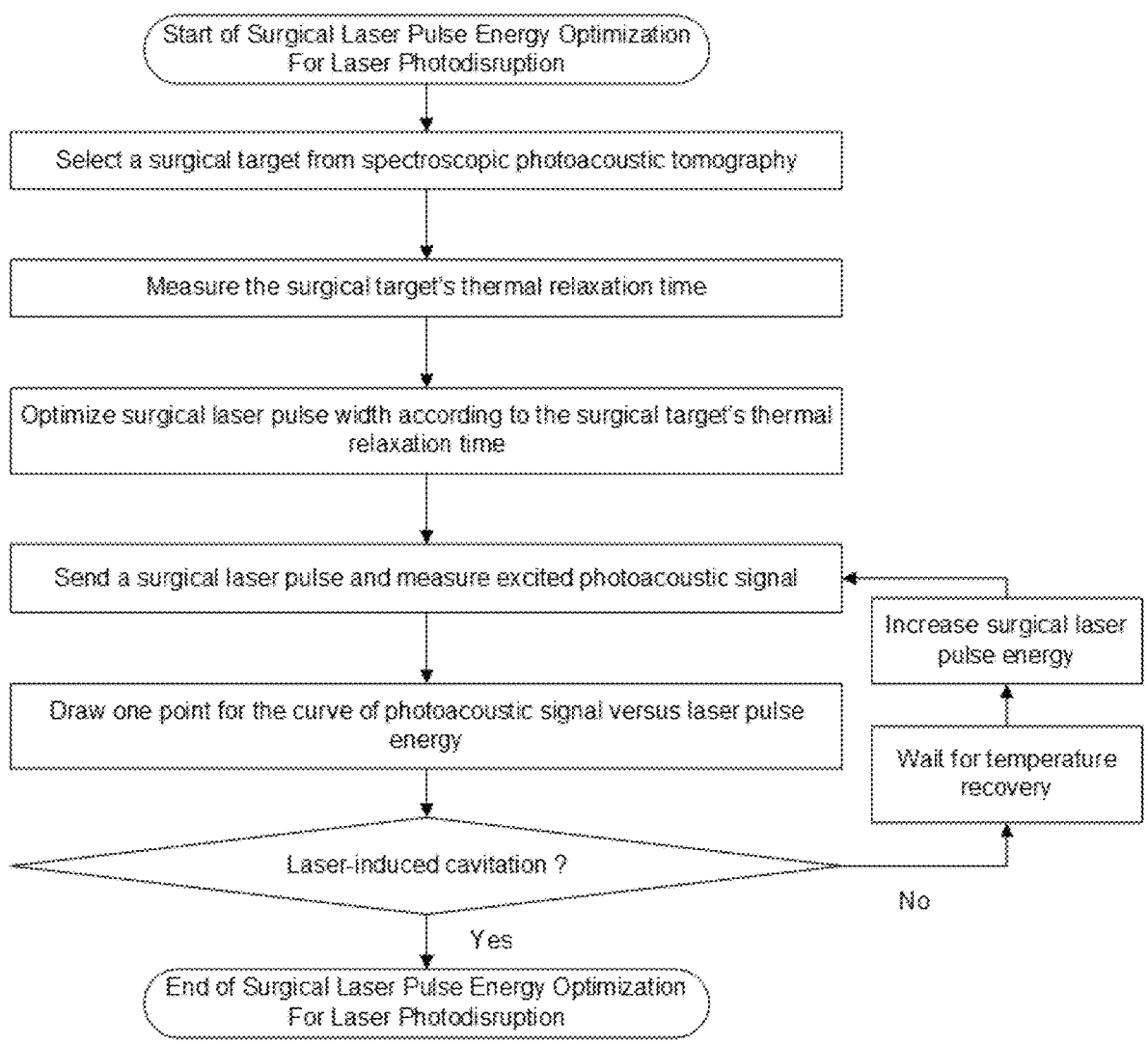
FIG. 16 shows an example of in vivo surgical laser pulse energy optimization for laser photodisruption during a laser surgery.

A distinct feature of laser photodisruption is the generation of acoustic shock-waves due to a laser-induced cavitation. We assume there is no need to further increase laser pulse energy once the acoustic shock-wave due to laser-induced cavitation is observed. For laser photodisruption in laser tattoo removal application, it is desirable to use a tunable surgical laser instead of a more advanced tunable dual-pulse (a surgical laser pulse followed by a delayed temperature-sensing laser pulse) surgical laser. FIG. 16 shows an example of in vivo surgical laser pulse energy optimization during a laser photodisruption SP surgery. The following procedure is designed for a laser SP surgery system whose surgical laser pulse width is short enough to effectively excite photoacoustic signals. We assume the laser wavelength is already optimized before laser pulse energy optimization. First, we select a surgical target with a 2-D, depth resolved tissue information excited by the surgical laser pulse and acquired by an acoustic detector; Second, we measure the surgical target's thermal relaxation time and optimize surgical laser pulse width according to the surgical target's thermal relaxation time; Third, we send a surgical laser pulse and measure excited photoacoustic signal; Fourth, we draw one point for the curve of photoacoustic signal versus laser pulse energy and determine whether there is an abrupt photoacoustic signal increase due to a laser-induced cavitation. If there is no abrupt photoacoustic signal increase, we can wait for the surgical target to recover its original body temperature, increase surgical laser pulse energy, and return to the third step. If an abrupt photoacoustic signal increase due to laser-induced cavitation is observed, the optimal laser pulse energy is achieved. The same technique in FIG. 16 applies to pulsed laser (coherent light source) SP surgical systems, other non-coherent pulsed light-source SP surgical systems, and other general radiation SP systems using a surgical pulsed radiation beam to heat up lesions in tissue or extraneous contrast agents attached to lesions in tissue, and excite photoacoustic waves from lesions in tissue or extraneous contrast agents attached to lesions in tissue.

Figure 17:
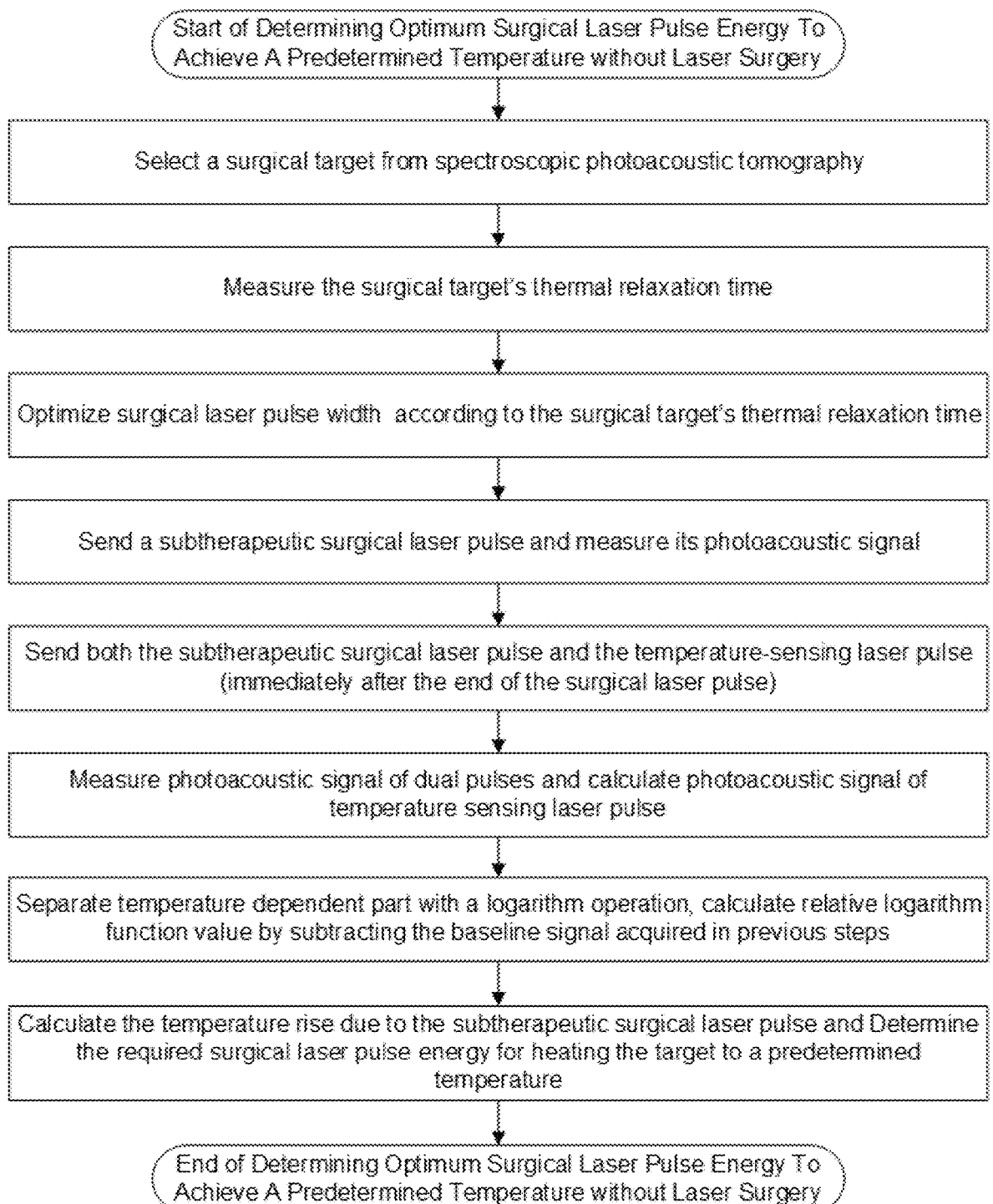
FIG. 17 shows an example of determining optimal surgical laser pulse energy to achieve a predetermined temperature without performing laser surgery.

The methods in FIGS. 15 and 16 provide real time control of surgical laser pulse energy during laser SP surgeries. However, it is possible to accurately determine the required surgical laser pulse energy for a surgical target to reach a predetermined temperature without actually performing laser surgery. FIG. 17 shows an example of determining optimal surgical laser pulse energy to achieve a predetermined temperature without performing laser surgery. We assume the laser wavelength is already optimized. First, we select a surgical target with a 2-D, depth resolved tissue information excited by the temperature-sensing laser pulse and acquired by an acoustic detector; Second, we optimize laser pulse width after measuring the surgical target's thermal relaxation time; Third, we send a subtherapeutic surgical laser pulse and detect its photoacoustic signal; Fourth, we send both a subtherapeutic surgical laser pulse and a temperature-sensing laser pulse, which is immediately after the end of the surgical laser pulse; Fifth, we measure photoacoustic signal excited by both the surgical laser pulse and the temperature-sensing laser pulse, and calculate the amplitude of the photoacoustic signal excited by the temperature-sensing laser pulse; Sixth, we separate temperature-dependent part with a logarithm operation, calculate a relative logarithm function value by subtracting the baseline signal acquired in previous steps; Finally, we calculate the temperature rise due to the subtherapeutic surgical laser pulse and determine the required surgical laser pulse energy for heating the target to a predetermined temperature. The same technique in FIG. 17 applies to pulsed laser (coherent light source) SP surgical systems, other non-coherent pulsed light-source SP surgical systems, high-intensity-focused-ultrasound therapy systems, and other general radiation SP systems using a surgical pulsed radiation beam to heat up lesions in tissue or extraneous contrast agents attached to lesions in tissue, and a pulsed or modulated temperature-sensing radiation beam to effectively excite photoacoustic waves from lesions in tissue or extraneous contrast agents attached to lesions in tissue.

Figure 18:
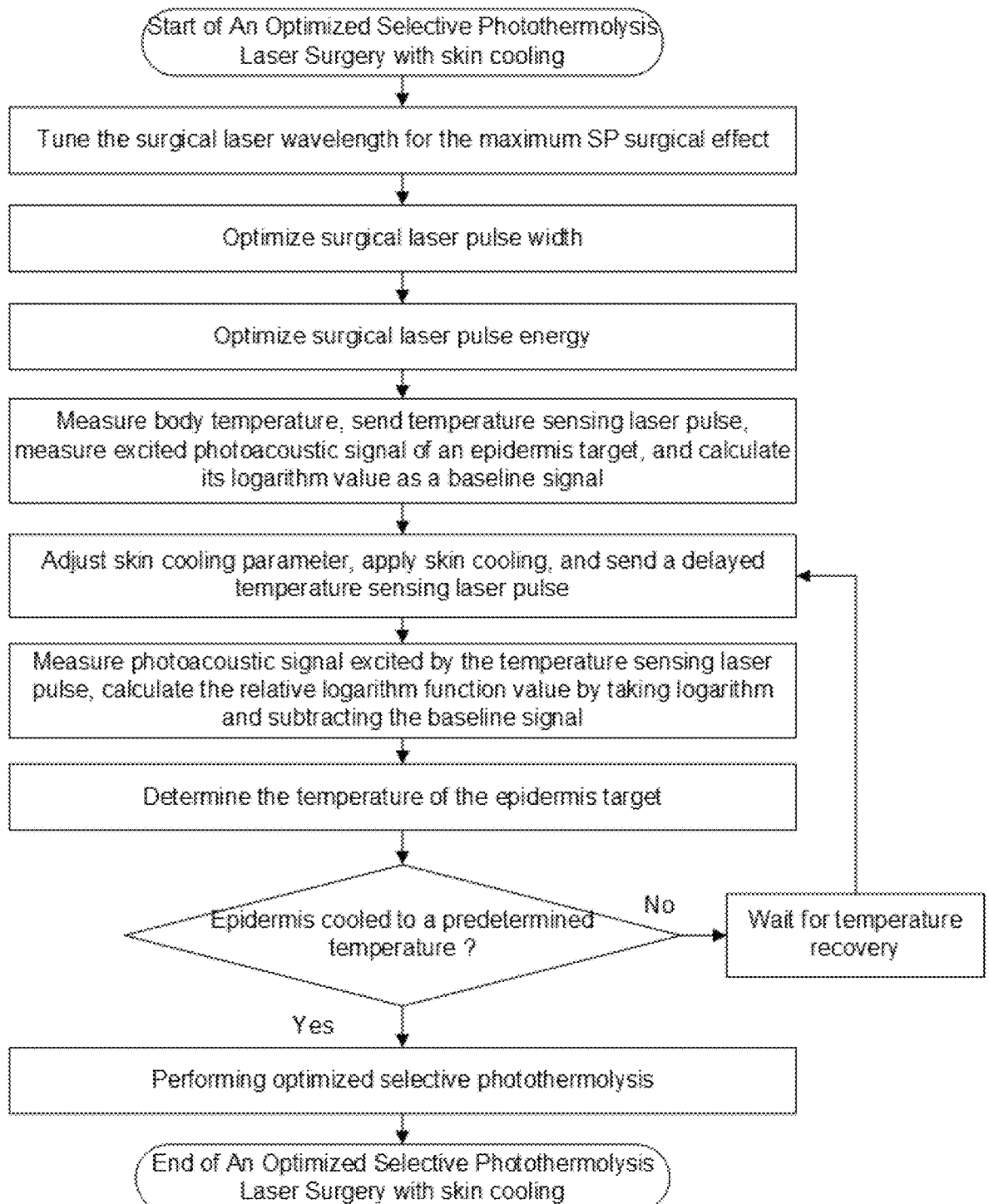
FIG. 18 shows an example of operations for an optimized selective photothermolysis laser surgery with skin cooling.

One potential usage of the acoustic detector is to provide in vivo temperature calibration for skin cooling devices that provide protections for skin epidermis layer in a laser SP surgery. Skin cooling is widely used in laser treatment of vascular malformation. Skin cooling can effectively prevent laser-induced cavitation in epidermis during laser tattoo removal as well. FIG. 18 shows an example of operations for an optimized laser SP surgery with skin cooling. First, we tune the surgical laser wavelength to maximize SP surgical effects; Second, we optimize the surgical laser pulse width according to the measured thermal relaxation time of the surgical target; Third, we optimize surgical laser pulse energy according to the expected surgical effects (photocoagulation or photodisruption); Fourth, we measure body temperature, send a temperature-sensing laser pulse, measure the amplitude of the excited photoacoustic signal of an epidermis target, and calculate its logarithm value as a baseline signal; Fifth, we adjust skin cooling parameter, apply skin cooling, and send a delayed temperature-sensing laser pulse; Sixth, we measure the amplitude of the photoacoustic signal excited by the temperature-sensing laser pulse, calculate the relative logarithm function value by taking logarithm and subtracting the baseline signal; Seventh, we determine the temperature of the epidermis target and whether the epidermis target is cooled to a predetermined temperature. If not, we wait for temperature recovery and return to the fifth step. If yes, we perform optimized SP surgery. The same technique in FIG. 18 applies to pulsed laser (coherent light source) SP surgical systems, other non-coherent pulsed light-source SP surgical systems, and other general radiation SP systems using a surgical pulsed radiation beam to heat up lesions in tissue or extraneous contrast agents attached to lesions in tissue, and a pulsed or modulated temperature-sensing radiation beam to effectively excite photoacoustic waves from lesions in tissue or extraneous contrast agents attached to lesions in tissue.

Techniques, apparatus and methods for optimizing selective photothermolysis laser surgery are disclosed. However, variations and enhancements of the described implementations, and other implementations can be made based on what is described.

REFERENCES CITED

| U.S. PATENT DOCUMENTS | |
|---|---|
| 5,840,023 A | Filed in January 1996 by Oraevsky et al. |
| 6,309,352 B1 | Filed in October 1998 by Oraevsky et al. |
| 2015/0216420 A1 | Filed in February 2015 by Oraevsky et al. |
| 4,303,343 | Filed in February 1980 by Patel et al. |
| 62/617,681 | Filed in January 2018 by Rao Bin. |
| 7,322,972 B2 | Filed in February 2003 by Viator et al. |
| 2017/0014317A1 | Filed in July 2016 by Youngbull et al. |
| 2002/0019625A1 | Filed in April 2001 by Zion Azar |
| 5,759,200 | Filed in September 1996 by Zion Azar |

FOREIGN PATENT DOCUMENTS WO 2013/033145A1 Filed in August 2011 by Nikolai et al.

OTHER PUBLICATIONS

Adams et al., "Thermal diffusivity and thickness measurements for solid samples utilizing the optoacoustic effect," The Analyst 102,678 (1977).
Barua et al., "Laser-tissue interaction in tattoo removal by Q-switched lasers ," J Cutan Aesthet Surg 8, 5-8 (2015).
Bernstein, "Laser Tattoo Removal," SEMINARS IN PLASTICS SURGERY 21, 175-192 (2007).
C. T. Andrew, "Applications of photoacoustic sensing techniques," Rev. Mod. Phys. 58, 381-431 (1986).
Cox et al., "Quantitative spectroscopic photoacoustic imaging: a review," *Journal of Biomedical Optics* 17 (6), 061202 (2012).

Esenaliev et al., "Real-time optoacoustic monitoring of temperature in tissues", Proc. SPIE 3601, Laser-Tissue Interaction X: Photochemical, Photothermal, and Photomechanical (1999).

Gary A. West, "Photoacoustic spectroscopy," Review of Scientific Instruments 54, 797 (1983).

Hordvik et al., "Photoacoustic technique for determining optical absorption coefficients in solids," Applied Optics 16, 101-107 (1977).

Larin et al., "Monitoring of temperature distribution in tissues with optoacoustic technique in real time", Proc. SPIE 3916, Biomedical Optoacoustics (2000).

Liu et al., "In vivo, high-resolution, three-dimensional Imaging of port wine stain microvasculature in human skin," Lasers in Surgery and Medicine 45, 626-632 (2013).

Maslov et al., "Optical-resolution photoacoustic microscopy for in vivo imaging of single capillaries", Optics Letters 33, 929-931 (2008).

Maslov et al., "In vivo dark-field reflection-mode photoacoustic microscopy," Optics Letters 30, 625-627 (2005).

Nelson et al., "Imaging blood flow in human port-wine stain in situ and in real time using optical Doppler tomography," *Arch Dermatol.* 137, 741-744 (2001).

Ortiz et al., "Port-wine stain laser treatment and novel approaches," Facial Plast Surg 28, 611-620 (2012).

Peach et al., "Colour shift following tattoo removal with Q-switched Nd-YAG laser (1064/532), " British Journal of Plastic Surgery 52, 482-487 (1999).

Rao et al., "Smart laser treatment of port-wine stain in children," NIH grant abstract, published on Aug. 1, 2012. http://grantome.com/grant/NIH/K99-AR062530-01.

Shah et al., "Photoacoustic imaging and temperature measurement for photothermal cancer therapy," *Journal of Biomedical Optics* 13 (3), 034024 (2008).

Viator et al., "In vivo port-wine stain depth determination with a photoacoustic probe," Appl. Opt. 42, 3215-3224 (2003).

Wang, "Prospects of photoacoustic tomography," Medical Physics 35, 5758 (2008).

Wenzel, "Current concepts in laser tattoo removal," Skin Therapy Letter 15, 3-5 (2010).

Zapka et al., "Noncontact optoacoustic monitoring of flame temperature profiles," Optics Letters 7, 477-479 (1982).

Zhang et al., "Backward-mode multiwavelength photoacoustic scanner using a planar Fabry-Perot polymer film ultrasound sensor for high-resolution three-dimensional imaging of biological tissues," Applied Optics 47, 561-577 (2008).

What is claimed is:

1. A method of non-invasively measuring Grüneisen parameters of a target tissue or medium surrounding a target as a function of temperature of the target via photoacoustic measurements, the method comprising the steps of:
   i: measuring an equilibrium temperature of the target tissue or medium surrounding the target prior to electromagnetic (EM) excitations of the target tissue;
   ii: measuring, via photoacoustic measurements, a baseline photoacoustic signal amplitude due to EM excitations from the target tissue at the equilibrium temperature;
   iii: heating the target tissue from the equilibrium temperature to a photodisruption point at 100° C. via EM excitations comprising a series of heating EM pulses;
   iv: while performing EM excitations, monitoring, via photoacoustic measurements, an increase in signal amplitude as a result of each of the series of heating EM pulses;
   v: ceasing EM excitations when the photoacoustic measurement of the signal amplitude shows an abrupt increase resulting from water vaporization at 100° C., the signal amplitude increase being indicative of cavitation effects in the target tissue or medium surrounding the target;
   vi: correcting photoacoustic signal amplitudes with the baseline photoacoustics signal amplitude, further processing the corrected photoacoustic signal amplitudes at a plurality of temperature points, from the equilibrium temperature to the photodisruption point, calculating calibrated Grüneisen parameters for the temperature points heated by the series of heating EM pulses, and outputting the resulting Grüneisen parameters of the target tissue or medium surrounding the target as a function of the temperature of the target at each point.

2. A non-invasive photoacoustic temperature measurement method that is based on Grüneisen parameters of a target tissue or medium surrounding the target as a function of the temperature of a target, as described in claim 1, further comprising the step of:
   non-invasively calibrating from the target tissue prior to the detection of a target temperature via photoacoustic, non-invasive monitoring during a therapy process.

\* \* \* \* \*